United States Patent
Schwartz et al.

(10) Patent No.: US 11,266,467 B2
(45) Date of Patent: Mar. 8, 2022

(54) SYSTEMS AND METHODS FOR REGISTRATION OF INTRA-BODY ELECTRICAL READINGS WITH A PRE-ACQUIRED THREE DIMENSIONAL IMAGE

(71) Applicant: Navix International Limited, Road Town (VG)

(72) Inventors: Yitzhack Schwartz, Haifa (IL); Eli Dichterman, Haifa (IL); Yizhaq Shmayahu, Ramat-HaSharon (IL)

(73) Assignee: Navix International Limited, Road Town (VG)

( * ) Notice: Subject to any disclaimer, the term of this patent is extended or adjusted under 35 U.S.C. 154(b) by 340 days.

(21) Appl. No.: 16/338,710

(22) PCT Filed: Oct. 25, 2017

(86) PCT No.: PCT/IB2017/056616
§ 371 (c)(1),
(2) Date: Apr. 2, 2019

(87) PCT Pub. No.: WO2018/078540
PCT Pub. Date: May 3, 2018

(65) Prior Publication Data
US 2020/0085504 A1 Mar. 19, 2020

Related U.S. Application Data

(60) Provisional application No. 62/412,324, filed on Oct. 25, 2016.

(51) Int. Cl.
*A61B 34/20* (2016.01)
*A61B 34/10* (2016.01)
(Continued)

(52) U.S. Cl.
CPC ............ *A61B 34/20* (2016.02); *A61B 5/0538* (2013.01); *A61B 5/063* (2013.01); *A61B 5/066* (2013.01);
(Continued)

(58) Field of Classification Search
CPC ..... A61B 5/0536; A61B 5/0538; A61B 5/065; A61B 5/068; A61B 5/285; A61B 5/287; A61B 5/4233; A61B 5/6852; G06T 15/00
See application file for complete search history.

(56) References Cited

U.S. PATENT DOCUMENTS

| | | | |
|---|---|---|---|
| 5,465,730 | A | 11/1995 | Zadehkoochak et al. |
| 5,553,611 | A | 9/1996 | Budd et al. |

(Continued)

FOREIGN PATENT DOCUMENTS

| | | |
|---|---|---|
| EP | 0974936 | 1/2000 |
| EP | 1767166 | 3/2007 |

(Continued)

OTHER PUBLICATIONS

International Preliminary Report on Patentability dated May 9, 2019 From the International Bureau of WIPO Re. Application No. PCT/IB2017/056616. (8 Pages).

(Continued)

*Primary Examiner* — Mark D Remaly

(57) ABSTRACT

There is provided a method of displaying a pre-acquired three dimensional (3D) image of at least a portion of an organ of a patient, the method comprising: receiving a plurality of electrical readings, each from a different electrode mounted on a catheter inside the portion of the organ of the patient, wherein the electrodes are mounted on the catheter at known distances from each other, transforming the plurality of electrical readings to a corresponding plurality of image points using a mapping transformation that (Continued)

transforms each electrical reading of the catheter from inside the portion of the organ of the patient to an anatomically corresponding image point in the 3D image based on the known distances, and displaying the 3D image with a marking of at least one of the plurality of image points.

30 Claims, 16 Drawing Sheets

(51) Int. Cl.
*A61B 5/0538* (2021.01)
*A61B 5/06* (2006.01)
*A61B 5/00* (2006.01)

(52) U.S. Cl.
CPC .......... *A61B 5/7207* (2013.01); *A61B 5/7253* (2013.01); *A61B 5/7425* (2013.01); *A61B 34/10* (2016.02); *A61B 2034/107* (2016.02); *A61B 2034/2048* (2016.02)

(56) References Cited

U.S. PATENT DOCUMENTS

| | | | |
|---|---|---|---|
| 5,662,108 | A | 9/1997 | Budd et al. |
| 5,697,377 | A | 12/1997 | Wittkampf |
| 6,240,307 | B1 | 5/2001 | Beatty et al. |
| 6,640,119 | B1 | 10/2003 | Budd et al. |
| 6,728,562 | B1 | 4/2004 | Budd et al. |
| 6,826,420 | B1 | 11/2004 | Beatty et al. |
| 6,939,309 | B1 | 9/2005 | Beatty et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,187,973 | B2 | 3/2007 | Hauck |
| 7,189,208 | B1 | 3/2007 | Beatty et al. |
| 7,996,060 | B2 | 8/2011 | Trofimov et al. |
| 2003/0018251 | A1† | 1/2003 | Solomon |
| 2007/0049817 | A1† | 3/2007 | Preiss |
| 2008/0190438 | A1 | 8/2008 | Harlev et al. |
| 2009/0171274 | A1 | 7/2009 | Harlev et al. |
| 2009/0262109 | A1 | 10/2009 | Markowitz et al. |
| 2009/0264778 | A1 | 10/2009 | Markovitz et al. |
| 2012/0059249 | A1 | 3/2012 | Verard et al. |
| 2012/0078129 | A1 | 3/2012 | Bailin |
| 2012/0150046 | A1 | 6/2012 | Watson et al. |
| 2014/0275991 | A1 | 9/2014 | Potter et al. |
| 2016/0045133 | A1* | 2/2016 | Balachandran .... A61B 18/1492 600/509 |
| 2016/0242667 | A1 | 8/2016 | Fay et al. |
| 2019/0336035 | A1 | 11/2019 | Dichterman et al. |
| 2020/0000368 | A1 | 1/2020 | Ben-Haim et al. |
| 2020/0289025 | A1 | 9/2020 | Dichterman et al. |
| 2021/0128009 | A1 | 5/2021 | Ben-Haim |

FOREIGN PATENT DOCUMENTS

| | | |
|---|---|---|
| JP | 2003/527164 | 9/2003 |
| WO | WO 98/01069 | 1/1998 |
| WO | WO 2006/055286 | 5/2006 |
| WO | WO 2008/097767 | 8/2008 |
| WO | WO 2010/129095 | 11/2010 |
| WO | WO 2011/142931 | 11/2011 |
| WO | WO 2012/092016 | 7/2012 |
| WO | WO2014/036439 | 3/2014 |
| WO | WO 2014/118535 | 8/2014 |
| WO | WO 2014/182822 | 11/2014 |
| WO | WO 2018/078540 | 5/2018 |
| WO | WO 2018/130974 | 7/2018 |
| WO | WO 2018/146613 | 8/2018 |
| WO | WO 2018/146613 A2 | 8/2018 |
| WO | WO 2019/034944 | 2/2019 |
| WO | WO 2019/035023 | 2/2019 |

OTHER PUBLICATIONS

International Search Report and the Written Opinion dated Feb. 1, 2018 From the International Searching Authority Re. Application No. PCT/IB2017/056616. (14 Pages).
Crospon "Esophageal Treatment by Esoflip®", Crospon, Product Sheet, 4 P., 2017.
Crospon "Flip® Technology", Crospon, Product Sheet, 6 P., 2017.
Myronenko et al. "Non-Rigid Point Set Registration: Coherent Point Drift", Advances in Neural Information Processing Systems, NIPS, 19: 1009-1016, 2009.
Official Action dated May 5, 2021 from the US Patent and Trademark Office Re. U.S. Appl. No. 16/476,875. (35 pages).
International Preliminary Report on Patentability dated Aug. 22, 2019 From the International Bureau of WIPO Re. Application No. PCT/IB2018/050784. (11 Pages).
International Preliminary Report on Patentability dated Jul. 25, 2019 From the International Bureau of WIPO Re. Application No. PCT/IB2018/050192. (8 Pages).
International Search Report and the Written Opinion dated Jan. 2, 2019 From the International Searching Authority Re. Application No. PCT/IB2018/056158. (16 Pages).
International Search Report and the Written Opinion dated May 9, 2018 From the International Searching Authority Re. Application No. PCT/IB2018/050192. (16 Pages).
International Search Report and the Written Opinion dated Sep. 25, 2018 From the International Searching Authority Re. Application No. PCT/IB2018/050784. (18 Pages).
International Search Report and the Written Opinion dated Nov. 30, 2018 From the International Searching Authority Re. Application No. PCT/IB2018/055344. (15 Pages).
Invitation to Pay Additional Fees, Communication Relating to the Results of the Partial International Search and the Provisional Opinion dated Jun. 26, 2018 From the International Searching Authority Re. Application No. PCT/IB2018/050784. (13 Pages).
Boston Scientific "Rhythmia™ Mapping System: Rhythmia Disposables Product Information: Intellamap Orion™ High Resolution Mapping Catheter", Boston Scientifc, 2 P., Sep. 2015.
Hilbert et al. "An Integrative Approach to Slow Pathway Modulation in AVNRT Using A Novel Ultra High-Density Electroanatomical Mapping System". Clinical Research in Cardiology, XP035518036, 104(8): 697-699. Published Online Mar. 31, 2015.
International Preliminary Report on Patentability dated Feb. 27, 2020 From the International Bureau of WIPO Re. Application No. PCT/IB2018/055344. (8 Pages).
International Preliminary Report on Patentability dated Feb. 27, 2020 From the International Bureau of WIPO Re. Application No. PCT/IB2018/056158. (8 Pages).

\* cited by examiner
† cited by third party

| Type# | Sub-Type# | MNF# | Dscp.# |
|---|---|---|---|
| Therapeutic | NAV | BW | THERMOCOOL SMARTTOUCH® SF Uni-Directional Catheter. |
| | | | THERMOCOOL SMARTTOUCH® SF Bi-Directional Catheter |
| | | | THERMOCOOL SMARTTOUCH® Uni-Directional Catheter |
| | | | THERMOCOOL SMARTTOUCH® Bi-Directional Catheter |
| | | | THERMOCOOL® SF NAV Uni-Directional Catheter |
| | | | THERMOCOOL® SF NAV Bi-Directional Catheter |
| | | | THERMOCOOL® SF NAV Uni-Directional Catheter with curve visualization |
| | | | THERMOCOOL® SF NAV Bi-Directional Catheter with curve visualization |
| | | | NAVISTAR® THERMOCOOL® Uni-Directional Catheter |
| | | | NAVISTAR® THERMOCOOL® Bi-Directional Catheter |
| | | | NAVISTAR® 4 mm Catheter |
| | | | NAVISTAR® DS Catheter |
| | | | NAVISTAR® RMT THERMOCOOL® Catheter |
| | | | NAVISTAR® RMT 4 mm Catheter |
| | NON-NAV | | THERMOCOOL® SF Uni-Directional Catheter |
| | | | THERMOCOOL® SF Bi-Directional Catheter |
| | | | EZ STEER® THERMOCOOL® Catheter |
| | | | EZ STEER® 4 mm Bi-Directional Catheter |
| | | | EZ STEER® DS Bi-Directional Catheter |
| | | | CELSIUS® THERMOCOOL® Uni-Directional Catheter |
| | | | CELSIUS® RMT THERMOCOOL® Catheter |
| | | | CELSIUS® 4 mm Catheter Thermocouple |
| | | | CELSIUS® 4 mm Catheter Thermistor |
| | | | CELSIUS® 4 mm Braided Tip Catheter |
| | | | CELSIUS FLTR™ 8 mm Uni-Directional Catheter |
| | | | CELSIUS FLTR™ 8 mm Bi-Directional Catheter |
| Diagnostic | NAV | | LASSO® 2515 NAV Variable Catheter |
| | | | LASSO® NAV Catheter |
| | | | DECANAV™ Catheter |

FIG. 5

| Type# | Sub-Type# | MNF# | Dscp.# |
|---|---|---|---|
| Therapeutic | NAV | SJ | TactiCath™ Contact Force Ablation Catheter, Sensor Enabled™ |
| | | | TactiCath™ Quartz Contact Force Ablation Catheter |
| | | | Contact™ Therapy™ Cool Path™ Duo Ablation Catheter Irrigated 4 mm Tip Thermocouple Quadripolar 7 F |
| | | | Cool Path™ Duo Ablation Catheter MediGuide Enabled™ Irrigated 4 mm Tip Thermocouple Quadripolar 8 F |
| | | | FlexAbility™ Ablation Catheter Sensor Enabled™ |
| | | | Safire™ Duo Bi-directional Ablation Catheter MediGuide Enabled™ Irrigated 4 mm TipThermocouple Quadripolar8 |
| | NON-NAV | | Therapy™ Ablation Catheters 4 & 8 mm Tip Thermistor Quadripolar 7F |
| | | | Therapy™ Ablation Catheters 4 & 8 mm Tip Thermocouple Quadripolar7 F |
| | | | Therapy™ Ablation Catheters 4 & 8 mm Tip Thermocouple Triflex Bi-directional Quadripolar 7 F |
| | | | Therapy™ Ablation Catheters 4 & 8 mm Tip Thermocouple Triflex Uni-directional Quadripolar 7 F |
| | | | Therapy™ Ablation Catheters 4 mm Tip Thermocouple 5 F |
| | | | Therapy™ Cool Flex™ Ablation Catheter Irrigated 4 mm Tip Thermocouple Quadripolar 7 F |
| | | | Therapy™ Cool Path™ Ablation Catheter Irrigated 2 & 4 mm Tip Quadripolar 7 F |
| | | | Therapy™ Cool Path™ Ablation Catheters 4 mm Tip Thermocouple Quadripolar 7 F |
| | | | Therapy™ Cool Path™ Duo Ablation Catheters 4 mm Tip Thermocouple Quadripolar 7 F |
| | | | Therapy™ Dual-8™ Ablation Catheters 8 mm Tip Dual Thermocouple Quadripolar 7 F |
| | | | FlexAbility™ Ablation Catheter |
| | NON-NAV NON-Irrigated | | Livewire™ TC Ablation Catheters4 & 8 mm Tip Universal Temperature Monitoring Quadripolar Uni-directional7 F |
| | | | Livewire™ TC Ablation Catheters4 mm Tip Universal Temperature Monitoring Quadripolar Bi-Directional7 F |
| | | | Livewire™ TC Ablation Catheters4 & 8 mm Tip Thermocouple Quadripolar Uni-directional7 F |
| | | | Safire™ Bi-directional Ablation Catheters4 & 8 mm Tip Universal Temperature Monitoring Quadripolar7 F |
| Diagnostic | LASSO | | eValuator™ Electrophysiology Catheters Quadripolar6 F |
| | | | Inquiry™ Electrophysiology Catheter Inquiry™ AFocus II™ (4 F Double Loop) Catheter 7F |
| | | | Inquiry™ Electrophysiology Catheter Inquiry™ AFocus™ Catheter 5 F |
| | | | Inquiry™ Electrophysiology Catheter Inquiry™ Optima™ PLUS (5 F Loop) Catheter 7 F |
| | | | Inquiry™ Electrophysiology Catheters Inquiry™ AFocus II™ EB Catheter 7 F |
| | NON-NAV | | Inquiry™ Electrophysiology Catheter Luma-Cath™ Catheter Decapolar7 F |

FIG. 5 Continued 1

| Type# | Sub-Type# | MNF# | Dscp.# |
|---|---|---|---|
| Therapeutic | | Boston S | BLAZER™ II Temperature Ablation Catheter |
| | | | BLAZER™ II Temperature Ablation Catheter Bidirectional Curve Options |
| | | | BLAZER™ II HTD (High Torque Distal) Temperature Ablation Catheter |
| | | | BLAZER™ II XP Temperature Ablation Catheter |
| | | | BLAZER™ OPEN-IRRIGATED Ablation Catheter |
| | | | BLAZER PRIME™ HTD Temperature Ablation Catheter |
| | | | BLAZER PRIME™ XP Temperature Ablation Catheter |
| | | | BLAZER PRIME™ Temperature Ablation Catheter Bidirectional Curve Options |
| | | | CHILLI II™ Cooled Ablation Catheter |
| | | | INTELLATIP MIFI™ XP Temperature Ablation Catheter |
| | | | INTELLANAV™ XP Ablation Catheter |
| | | | INTELLANAV™ OPEN-IRRIGATED Ablation Catheter |
| | | | INTELLANAV MIFI™ XP Ablation Catheter |
| Diagnostic | Fixed | | VIKING™ Fixed Curve Diagnostic Catheter (5F-6F) |
| | | | VIKING™ SOFT TIP Fixed Curve Diagnostic Catheter (6F) |
| | | | TANGO™ Fixed Curve Diagnostic Catheter (5F) |
| | | | WOVEN Fixed Curve Diagnostic Catheter (4F-7F) |
| | | | WOVENFLEXIE™ Fixed Curve Diagnostic Catheter (5F-6F) |
| | | | ORBITER™ Fixed Curve Diagnostic Catheter (6F) |
| | | | ORBITER™ High-Torque Fixed Curve Diagnostic Catheter (6F) |
| | Steerable | | Diagnostic Steerable Curve Options |
| | | | BLAZER™ DX-20 Bidirectional Duodecapolar Diagnostic Catheter |
| | | | BLAZER™ DX-20 Bidirectional Duodecapolar Diagnostic Catheter and Curve Options |
| | | | DYNAMIC TIP™ Steerable Diagnostic Catheter |
| | | | DYNAMIC XT™ Steerable Diagnostic Catheter |

FIG. 5 Continued 2

| Type# | Sub-Type# | MNF# | Dscp.# |
|---|---|---|---|
| | | Biotronik | |
| Therapeutic | Irrigated | | AlCath Flux Red G eXtra-Advanced irrigated GoldTip ablation catheter |
| | | | AlCath Flux Red G eXtra-Advanced irrigated tip ablation catheter |
| | NON-Irrigated | | AlCath Flutter Flux G eXtra-3.5 mm GoldTip ablation catheter |
| | | | AlCath Flutter Flux LT G-8mm GoldTip ablation catheter |
| | | | AlCath LT G FullCircle 8mm GoldTip ablation catheter |
| | | | AlCath LT FullCircle 8mm tip ablation catheter |
| | | | AlCath G FullCircle 4mm GoldTip ablation catheter |
| | | | AlCath FullCircle 4mm tip ablation catheter |
| | | | Trignum Flux G Irrigated GoldTip ablation catheter for magnetic navigation |
| Diagnostic | | | MultiCath 4-Pole |
| | | | MultiCath 5-Pole |
| | | | MultiCath 6-Pole |
| | | | MultiCath 10-Pole |
| | | | Woxx 4-Pole Multipolar high-end diagnostic catheter |
| | | | Woxx 10-Pole Multipolar high-end diagnostic catheter |
| | Steerable | | ViaCath 4 Steerable |
| | | | ViaCath 8 Steerable |
| | | | ViaCath 10 Steerable |
| | | | ViaCath 20 Steerable |
| | Lasso | | Lexx Atraumatic stability. Reliable mapping |

FIG. 5 Continued 3

| Type# | Sub-Type# | MNF# | Dscp.# |
|---|---|---|---|
| | | MicroPort | |
| Therapeutic | NON-Irrigated | | FireMagic™ Cardiac RF Ablation Catheter |
| | NAV - Irrigated (Columbus™ system) | | FireMagic™ 3D Irrigated Ablation Catheter |
| Diagnostic | | | EasyFinder™ Electrophysiology Diagnostic Catheter |
| | Lasso | | EasyLoop™ Circular Mapping Catheter |
| | | J-Cath | |
| Therapeutic | NON-Irrigated | | Ablaze Series single and Bi-direction |
| Diagnostic | CS | | Epstar snake 6/10P |
| | HIS | | Epstar HIS-RV Fixed |
| | Lasso | | Epstar Libero |
| | | Khelix | |
| Therapeutic | Irrigated | | KHELIX™ ABLATION EP CATHETER |
| Diagnostic | Lasso | | KHELIX™ LOOP EP CATHETERS 15/20mm |
| | | | KHELIX™ STEERABLE EP CATHETERS |
| | | | KHELIX™ FIXED EP CATHETERS |
| | | Lepu | |
| Therapeutic | Irrigated ???? | | Eel Cath™ Ablation |
| Diagnostic | CS/HIS | | Eel Cath™ Diagnostic |
| | Lasso | | Eel Cath™ Circular Mapping Diagnostic |
| | | Synaptic | |
| Therapeutic | Irrigated | | Rithm Cool Irrigated TIP Ablation Catheter |
| | Irrigated | | AquaSense® Micro Infusion Irrigated Tip Ablation Catheter |

FIG. 5 Continued 4

| Type# | Sub-Type# | MNF# | Dscp.# | MNF-PN# |
|---|---|---|---|---|
| Ablation | NAV-Irrigated | BW | NAVISTAR® THERMOCOOL® Uni-Directional Catheter D | 34H-37M |
| | | | NAVISTAR® THERMOCOOL® Uni-Directional Catheter F | 34H-57M |
| | | | NAVISTAR® THERMOCOOL® Uni-Directional Catheter J | 34H-J7M |
| | | | NAVISTAR® THERMOCOOL® Uni-Directional Catheter C | 34H27M |
| | | | THERMOCOOL® SF NAV Uni-Directional Catheter D | D131802 |
| | | | THERMOCOOL® SF NAV Uni-Directional Catheter F | D131803 |
| | | | THERMOCOOL SMARTTOUCH® SF Uni-Directional Catheter D | D134701 |
| | | | THERMOCOOL SMARTTOUCH® SF Uni-Directional Catheter F | D134702 |
| | | | THERMOCOOL SMARTTOUCH® Uni-Directional Catheter D | D133601 |
| | | | THERMOCOOL SMARTTOUCH® Uni-Directional Catheter F | D133602 |
| Diagnostic | Non-NAV LASSO | | LASSO® Decapolar Catheter D 4.5mm spacing/15mm loop | 35O26R |
| | | | LASSO® Decapolar Catheter D 6mm spacing/20mm loop | 35O36R |
| | Non-NAV CS | | PARAHISIAN® Catheter | 36L00Q |

FIG. 5 Continued 5

LASSO

- EP•XT™ Steerable Diagnostic Catheter
- ORBITER™ ST Steerable Diagnostic Catheter
- POLARIS X™ Steerable Decapolar Mapping Catheter
- RADIA™ Bidirectional Steerable Diagnostic Catheter
- RADIA™ Bidirectional Steerable Diagnostic Catheter and Curve Options
- STEEROCATH-DX™ Bidirectional Steerable Diagnostic Catheter
- ORBITER™ PV Variable Loop Mapping Catheter

FIG. 5 Continued 6

Inquiry™ Electrophysiology Catheters Octapolar 5 F
Inquiry™ Electrophysiology Catheter Pentapolar 5 F
Inquiry™ Electrophysiology Catheter Octapolar 5 F
Inquiry™ Electrophysiology Catheters Octapolar 6 F
Inquiry™ Electrophysiology Catheters Quadripolar 4 F
Inquiry™ Electrophysiology Catheters Quadripolar 5 F
Inquiry™ Electrophysiology Catheters Decapolar 4 F
Inquiry™ Electrophysiology Catheters Decapolar 5 F
Inquiry™ Electrophysiology Catheters Quadripolar 6 F
Inquiry™ Electrophysiology Catheters Decapolar 6 F
Inquiry™ Electrophysiology Catheters Decapolar 5 F
Inquiry™ Electrophysiology Catheters Decapolar 6 F
Inquiry™ Electrophysiology Catheters Hexapolar 6 F
Inquiry™ Electrophysiology Catheters Octapolar 6 F
Inquiry™ Electrophysiology Catheters Quadripolar 4 F
Inquiry™ Electrophysiology Catheters Quadripolar 5 F
Inquiry™ Electrophysiology Catheters Quadripolar 6 F
Inquiry™ Electrophysiology Catheters H-Curve 7 F Decapolar
Inquiry™ Electrophysiology Catheters H-Curve 7 F Duo-Decapolar and 24-Pole
Inquiry™ Electrophysiology Catheters Luma-Cath™ Catheters Bipolar 7 F
Inquiry™ Electrophysiology Catheters Ten Ten™ Catheter 7 F Livewire™ Electrophysiology Catheter Hexapolar 7 F
Livewire™ Electrophysiology Catheter Octapolar 7 F
Livewire™ Electrophysiology Catheter Decapolar 7 F
Livewire™ Electrophysiology Catheter Decapolar CSL™ Bi-directional 6 F
Livewire™ Electrophysiology Catheter Dual-Purpose Duo-Decapolar (20 electrodes) 7 F
Livewire™ Electrophysiology Catheter Octapolar 5 F
Livewire™ Electrophysiology Catheters Decapolar 5 F
Livewire™ Electrophysiology Catheters Decapolar 6 F
Livewire™ Electrophysiology Catheters Duo-Decapolar (20 electrodes) 7 F

FIG. 5 Continued 7

NAV

Livewire™ Electrophysiology Catheters Hexapolar 5 F
Livewire™ Electrophysiology Catheters Octapolar 6 F
Livewire™ Electrophysiology Catheters Quadripolar 6 F
Livewire™ Electrophysiology Catheters Quadripolar 7 F
Livewire™ Diagnostic Catheter MediGuide Enabled™

Supreme™ Electrophysiology Catheters Hexapolar 6 F
Supreme™ Electrophysiology Catheters Quadripolar 4 F
Supreme™ Electrophysiology Catheter Bipolar with Connector Leads 5 F
Supreme™ Electrophysiology Catheter Hexapolar (Unipolar Recording) 5 F
Supreme™ Electrophysiology Catheters Quadripolar 6 F
Supreme™ Electrophysiology Catheters Quadripolar with Connector Leads 6 F
Supreme™ Electrophysiology Catheters Decapolar 4 F
Supreme™ Electrophysiology Catheters Decapolar CSL™ 5 F
Supreme™ Electrophysiology Catheters Hexapolar 4 F
Supreme™ Electrophysiology Catheters Hexapolar 5 F
Supreme™ Electrophysiology Catheters Hexapolar (Unipolar Recording) 6 F
Supreme™ Electrophysiology Catheters Quadripolar 5 F
Supreme™ Electrophysiology Catheters Bipolar with Connector Leads 6 F

FIG. 5 Continued 8

| | |
|---|---|
| NON-NAV Auto-ID | LASSO® Decapolar Catheter |
| | LASSO® Duo-Decapolar Catheter |
| | WEBSTER® CS Uni-Directional Catheter |
| | WEBSTER® CS Bi-Directional Catheter |
| | WEBSTER® Quadrapolar Catheter Deflectable |
| | WEBSTER® Decapolar Catheter Deflectable |
| | WEBSTER® HIS Catheter |
| | WEBSTER® Quadrapolar Catheter Fixed |
| | WEBSTER® Decapolar Catheter Fixed |
| NON-NAV NON-Auto-ID | LASSO® 2515 Variable Mapping Catheter |
| | LASSO® Mapping Catheter |
| | WEBSTER® CS Bi-Directional Catheter |
| | WEBSTER® Octopolar Catheter Deflectable |
| | WEBSTER® Hexapolar Catheter Deflectable |
| | WEBSTER® Quadrapolar Catheter Deflectable |
| | WEBSTER® Decapolar Catheter Deflectable |
| | WEBSTER® Decapolar Catheter Fixed |
| | WEBSTER® Hexapolar Catheter Fixed |
| | WEBSTER® Quadrapolar Catheter Fixed |
| | WEBSTER® Duo-Decapolar Catheter |
| | HALO® XP Tricuspid Mapping Catheter |
| | ISMUS® Catheter |
| | AVAIL® Bipolar Fixed Shape Catheter |
| | AVAIL® Quadrapolar Fixed Shape Catheter |
| | CRISTACATH® Catheter |
| | PARAHISIAN® Catheter |

FIG. 5 Continued 9

SYSTEMS AND METHODS FOR REGISTRATION OF INTRA-BODY ELECTRICAL READINGS WITH A PRE-ACQUIRED THREE DIMENSIONAL IMAGE

RELATED APPLICATIONS

This application is a National Phase of PCT Patent Application No. PCT/IB2017/056616 having International filing date of Oct. 25, 2017, which claims the benefit of priority under 35 USC § 119(e) of U.S. Provisional Patent Application No. 62/412,324 filed on Oct. 25, 2016. The contents of the above applications are all incorporated by reference as if fully set forth herein in their entirety.

BACKGROUND

The present invention, in some embodiments thereof, relates to image registration and, more specifically, but not exclusively, to systems and methods for registration of electrical readings obtained from an intra-body location with a pre-acquired three dimensional image including the intra-body location.

Traditional intra-body navigation methods rely on real-time x-ray imaging (e.g., fluoroscopy) to help the operator determine the location of the catheter within the body of the patient. The operator may use the x-ray images to position the catheter within an organ (e.g., the heart) for performing a procedure (e.g., radiofrequency ablation).

Methods have been developed to reduce the fluoroscopic time (e.g., to reduce radiation exposure) by relying on other mechanisms to help navigate the catheter. However, such methods are generally not accurate enough for positioning the catheter within a defined tolerance for safely performing procedures, and/or still rely on a significant amount of real-time x-ray imaging (and hence radiation exposure).

SUMMARY

According to a first aspect, a method of displaying a pre-acquired three dimensional (3D) image of at least a portion of an organ of a patient, comprises: receiving a plurality of electrical readings, each from a different electrode mounted on a catheter inside the portion of the organ of the patient, wherein the electrodes are mounted on the catheter at known distances from each other, transforming the plurality of electrical readings to a corresponding plurality of image points using a mapping transformation that transforms each electrical reading of the catheter from inside the portion of the organ of the patient to an anatomically corresponding image point in the 3D image based on the known distances, and displaying the 3D image with a marking of at least one of the plurality of image points.

According to a second aspect, a system for displaying a pre-acquired three dimensional (3D) image of at least a portion of a heart of a patient, comprises: an electrical interface for receiving at least one electrical reading from an electrode mounted on a catheter inside the portion of the organ of the patient, a program store storing code, and at least one processor coupled to the electrical interface and the program store for implementing the stored code, the code comprising: code to transform the at least one electrical reading to an image point in the pre-acquired 3D image using a mapping transformation that transforms each electrical reading of the catheter from inside the portion of the organ of the patient to an anatomically corresponding image point in the pre-acquired 3D image, and code to display the pre-acquired 3D image with a marking at the image point.

According to a third aspect, a computer program product comprising a non-transitory computer readable storage medium storing program code thereon for implementation by at least one processor of a computing device, for displaying a pre-acquired three dimensional (3D) image of at least a portion of an organ of a patient, comprises: program instructions to receive at least one electrical reading from an electrode mounted on a catheter inside the portion of the organ of the patient, program instructions to transform the at least one electrical reading to an image point in the pre-acquired 3D image using a mapping transformation that transforms each electrical reading of the catheter from inside the portion of the organ of the patient to an anatomically corresponding image point in the pre-acquired 3D image, and program instructions to display the pre-acquired 3D image with a marking at the image point.

According to a fourth aspect, a method of displaying a pre-acquired three dimensional (3D) image of at least a portion of an organ of a patient, the method comprises: receiving an electrical reading from an electrode mounted on a catheter inside the portion of the organ of the patient, transforming the electrical reading to an image point in the pre-acquired 3D image using a mapping transformation that transforms each electrical reading of the catheter from inside the portion of the organ of the patient to an anatomically corresponding image point in the pre-acquired 3D image, and displaying the pre-acquired 3D image with a marking at the image point.

The systems and/or methods (e.g., code instructions executed by one or more processors) described herein address the technical problem of mapping the real-time, actual physical location of a catheter located within the body of a patient (e.g., within the heart, within a chamber of the heart, within the vasculature) to a corresponding anatomically correct point(s) on a pre-acquired image (e.g., a three dimensional image). In particular, the technical problem relates to correctly mapping the actual physical location of the catheter to the pre-acquired image during motion of the organ, for example, beating of the heart, and/or patient respiratory related movements. High accuracy of the actual location of the catheter within the body of the patient improves treatments using the catheter, for example, by helping the operator deliver treatment to a certain anatomical location more accurately.

The registration described herein may be performed relative to the pads (e.g., positioned on the skin of the patient), for example, in comparison to other registration methods which use inertial coordinates, in which the indication of catheter presented on the image moves as the catheter moves in respect to the room, even if the catheter is static in respect of the moving organ, the indication of the catheter may appear, according to some embodiments of the present invention, physically still on the screen.

Some conventional registration methods rely on manual user input for marking the correspondence between locations on the image and the body (e.g., by physically touching the body of the patient and the corresponding location on the image). This manual user input is used to generate the mapping between the image and the readings from the catheter. However, such mappings remain constant, and cannot adapt to changes and/or movement in the body that may occur during navigation, for example, volume changes in the heart due to hydration changes. In contrast, using the systems and/or methods described herein, the location of the indication of the catheter relative to the anatomy of the heart remains fixed, even as the heart changes size or location (e.g., due to increased hydration fluid or decreased hydration fluid, due to patient postural changes, and/or due to the cardiac cycle). For example, the indication of the catheter may appear static on the display as the heart increases or decreases in volume, since the indication of the catheter remains fixed relative to the same anatomical location.

The systems and/or methods described herein automatically register, during the procedure, positions within a lumen of an organ (e.g., chambers and/or vessels of the heart) that have been identified on a 3D and/or 4D image taken before the procedure began. The registration is performed with precision that is good enough to provide for targeting positions during the procedure. For example, in comparison to existing methods that rely on manual registration of pre-acquired images and result in poor precision that leads to inaccurate targeting. For example, the precision provided by embodiments of the current invention may be better than ±10 mm, without requiring any manual registration, while current methods that do require manual registration obtain accuracies of about ±20 mm with users that are regularly trained to provide manual registration, and up to ±7 mm with users that are highly trained to provide manual registration, and provided the manual registration is allowed about 20 to 30 minutes (to manually register 13-20 point pairs). In some embodiments of the present invention, these 20 to 30 minutes may be replaced by about 2 minutes of data collection and less than one minute of computation, even without employing a trained user.

It is noted that other registration methods that map electrical readings to pre-acquired anatomical images of the body of the patient are unable to perform correctly (e.g., within a predefined tolerance requirement) in cases of movement, since such methods are designed for registration of still images. The systems and/or methods described herein (e.g., the transformation code instructions, i.e., code instructions, that when executed by one or more processors carry out a transformation of one or more of the embodiments disclosed herein) are able to maintain anatomical correspondence of the electrical readings to image point(s) on the pre-acquired image, accounting for the movements of the organ, such as beating heart, breathing effects, patient movements, and changes in fluid volume of the patient.

The systems and/or methods (e.g., code instructions executed by one or more processors) described herein improve an underlying technical process within the technical field of image processing and/or image registration. The systems and/or methods described herein improve the process of mapping the location of electrode(s) located on a catheter (positioned within the body), to anatomically corresponding image point(s) on a pre-acquired image, which may be a pre-acquired 3D image, while the organ and/or tissues (from the body portion where the catheter is located) are moving.

The systems and/or methods described herein (e.g., code instructions executed by one or more processors) improve performance of the computing device executing the transformation code (that transforms the electrical reading(s) to the anatomically corresponding image point(s)) and/or other code instructions described herein (e.g., code instructions that dynamically generate a new transformation function). The improvement in performance is obtained by reducing the processing time, processing resources, and/or memory resources to compute the transformation, and/or compute the transformation function (e.g., transformation code), to achieve the anatomically correct transformation described herein. For example, manual markings between the actual location of the catheter within the body and the corresponding location on the image may be reduced or prevented. In another example, fluoroscopic time to obtain real-time x-ray images of the catheter within the body (which are registered to the pre-acquired 3D image) is reduced or omitted, since the registration to the pre-acquired 3D image is accurately and/or correctly performed using the electrical readings.

The systems and/or methods described herein (e.g., code instructions executed by one or more processors) are tied to physical real-life components, for example, using electrical readings obtained from a physical electrode located on a catheter. The computed anatomical corresponding image point(s) is presented on the pre-acquired image on a physical display.

The systems and/or methods described herein provide a unique, particular, and advanced technique of mapping electrical readings obtained from inside the body of a patient (e.g., using one or more electrodes located on a catheter) to anatomical corresponding point(s) on a pre-acquired 3D image.

Accordingly, the systems and/or methods described herein are inextricably tied to computer technology, to overcome an actual technical problem arising in image processing, in particular image registration, to help a user more accurately navigate a catheter within the body of a patient (e.g., within the heart) and/or help a user more accurately use the catheter to perform a treatment within the body of the patient.

In a further implementation form of the first, second, third, and fourth aspects, the location of the at least one of the plurality of image points is maintained relative to the 3D image during changes to the location of the electrodes relative to an external reference coordinate system, if the location of the electrodes does not change in relation to the anatomy of the at least a portion of the organ.

In a further implementation form of the first, second, third, and fourth aspects, the mapping transformation is computed independently of a static inertial coordinate system and of manually positioned landmark points.

In a further implementation form of the first, second, third, and fourth aspects, the electrical readings from the different electrodes mounted on the catheter are received simultaneously with each other.

In a further implementation form of the first, second, third, and fourth aspects, the different electrodes mounted on the catheter are mounted along a longitudinal axis of the catheter at a distal end region of the catheter.

In a further implementation form of the first, second, third, and fourth aspects, receiving an electrical reading comprises receiving a reading of electrical voltage.

In a further implementation form of the first, second, third, and fourth aspects, the method further comprises and/or the system further includes code for and/or the computer program product includes additional instructions for, and/or the method further comprises receiving a new electrical reading, transforming the new electrical reading to a new anatomically corresponding image point using the mapping transformation, and displaying the 3D image with a marking of the new anatomically corresponding image point.

In a further implementation form of the first, second, third, and fourth aspects, the mapping transformation is a transformation generated based on electrical readings all from a first part of the organ, and the new electrical reading is from a second part of the organ, different from the first part of the heart.

In a further implementation form of the first, second, third, and fourth aspects, the organ comprises a heart and each of the first and second parts of the heart is selected from the group consisting of: RA, LA, RV, LV, and aorta.

In a further implementation form of the first, second, third, and fourth aspects, the method further comprises and/or the system further includes code for and/or the computer program product includes additional instructions for, and/or the method further comprises receiving a new electrical reading, generating a new mapping transformation using the new electrical reading, transforming the new electrical reading to a new anatomically corresponding image point using the new mapping transformation, and displaying the 3D image with a marking at the new image point.

In a further implementation form of the first, second, third, and fourth aspects, the mapping transformation is generated based on a probabilistic correspondence model that defines the correspondence between the electrical points and points of the pre-acquired image as a probability.

In a further implementation form of the first, second, third, and fourth aspects, the probabilistic correspondence model is optimized while respecting the known distances between the electrodes that acquired the electrical readings.

In a further implementation form of the first, second, third, and fourth aspects, the optimization is performed based on quasi-neutral optimization methods.

In a further implementation form of the first, second, third, and fourth aspects, the mapping transformation is generated using a non-rigid registration algorithm.

In a further implementation form of the first, second, third, and fourth aspects, the mapping transformation is generated by performing: receiving image data representing the 3D image, receiving electrical readings from the catheter at multiple points inside the organ of the patient, and generating the mapping transformation based on the image data and the electrical readings.

In a further implementation form of the first, second, third, and fourth aspects, the mapping transformation is generated by performing: receiving electrical readings from the catheter at multiple points inside the organ of the patient, receiving estimations of electrical reading data for points inside the 3D image, and generating the mapping transformation based on the electrical readings, and the estimations of electrical reading data.

In a further implementation form of the first, second, third, and fourth aspects, the mapping transformation is generated based on a non-rigid transformation algorithm to map electrical readings from the catheter to the estimations of electrical reading data, and/or using a non-rigid transformation algorithm to map the estimations of electrical reading data to the electrical readings from the catheter.

In a further implementation form of the first, second, third, and fourth aspects, the estimations of electrical reading data are based on a simulation, the simulation being based on the 3D image.

In a further implementation form of the first, second, third, and fourth aspects, receiving an electrical reading comprises receiving a reading of electrical impedance.

In a further implementation form of the first, second, third, and fourth aspects, the method further comprises and/or the system further includes code for and/or the computer program product includes additional instructions for, and/or the method further comprises identifying wall points in the organ based on the impedance, and wherein the mapping transformation maps wall points in the organ to wall points in the 3D image.

In a further implementation form of the first, second, third, and fourth aspects, the method further comprises and/or the system further includes code for and/or the computer program product includes additional instructions for, and/or the method further comprises monitoring breathing movements of the patient, and correcting the electrical reading from the electrode mounted on the catheter inside the portion of the organ of the patient based on the breathing movements to obtain corrected electrical readings.

In a further implementation form of the first, second, third, and fourth aspects, transforming electrical readings comprises transforming a plurality of corrected electrical readings.

In a further implementation form of the first, second, third, and fourth aspects, the electrical readings include readings of potential difference between the electrode inside the organ and pad-electrodes attached to the outer surface of the patient.

In a further implementation form of the first, second, third, and fourth aspects, electrical readings are normalized to a potential difference between two of the pad-electrodes to obtain normalized electrical readings, and transforming the electrical readings includes transforming the normalized electrical readings.

In a further implementation form of the first, second, third, and fourth aspects, the method further comprises and/or the system further includes code for and/or the computer program product includes additional instructions for, and/or the method further comprises receiving electrical readings from multiple electrodes mounted on a static catheter inside a defined first organ-region of the patient, generating a mapping function mapping the electrical readings received from the multiple electrodes mounted on the static catheter to points in the 3D image, the points being in a part of the 3D image that images the first organ-region, and using the mapping function to generate the mapping transformation that transforms an electrical reading of the catheter from inside a second organ-region of the patient to an anatomically corresponding image point in the 3D image.

In a further implementation form of the first, second, third, and fourth aspects, the first-organ region comprises a coronary sinus of a heart and the second-organ region comprises another lumen of the heart.

In a further implementation form of the first, second, third, and fourth aspects, the method further comprises and/or the system further includes code for and/or the computer program product includes additional instructions for, and/or the method further comprises presenting a graphical overlay at a predefined anatomical location of the pre-acquired 3D image, and presenting the marking relative to the graphical overlay.

In a further implementation form of the first, second, third, and fourth aspects, the graphical overlay is a target defining at least one optimal treatment zone.

In a further implementation form of the first, second, third, and fourth aspects, the transforming is preformed based on the electrical readings with no use of manual registration between electrical readings and image points.

In a further implementation form of the first, second, third, and fourth aspects, the method further comprises and/or the system further includes code for and/or the computer program product includes additional instructions for, and/or the method further comprises correcting the pre-acquired 3D image according to the electrical readings, wherein the imaged portion of the organ of the corrected pre-acquired 3D image corresponds to the actual current anatomy of the imaged portion of the organ from which the electrical readings are obtained.

In a further implementation form of the first, second, third, and fourth aspects, the correction of the pre-acquired 3D image is performed so that a distance between two given electrodes is constant across the corrected 3D image.

In a further implementation form of the first, second, third, and fourth aspects, portions of the pre-acquired 3D image, imaging tissue external to the portion of the organ where the electrical readings are obtained are transformed according to the electrical readings obtained from the inside of the portion of the organ where the electrical readings are obtained.

In a further implementation form of the second, and fourth aspects, the system further includes code for and/or the method further comprises receiving a plurality of electrical readings, each from a different electrode mounted on the catheter, wherein the electrodes are mounted on the catheter at known distances from each other, and transforming the plurality of electrical readings to a corresponding plurality of image points using a mapping transformation that transforms each electrical reading of the catheter from inside the portion of the organ of the patient to an anatomically corresponding image point in the 3D pre-acquired image based on the known distances.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5 includes a list of exemplary catheters, in accordance with some embodiments of the invention.

DESCRIPTION OF SPECIFIC EMBODIMENTS OF THE INVENTION

Figure 1:
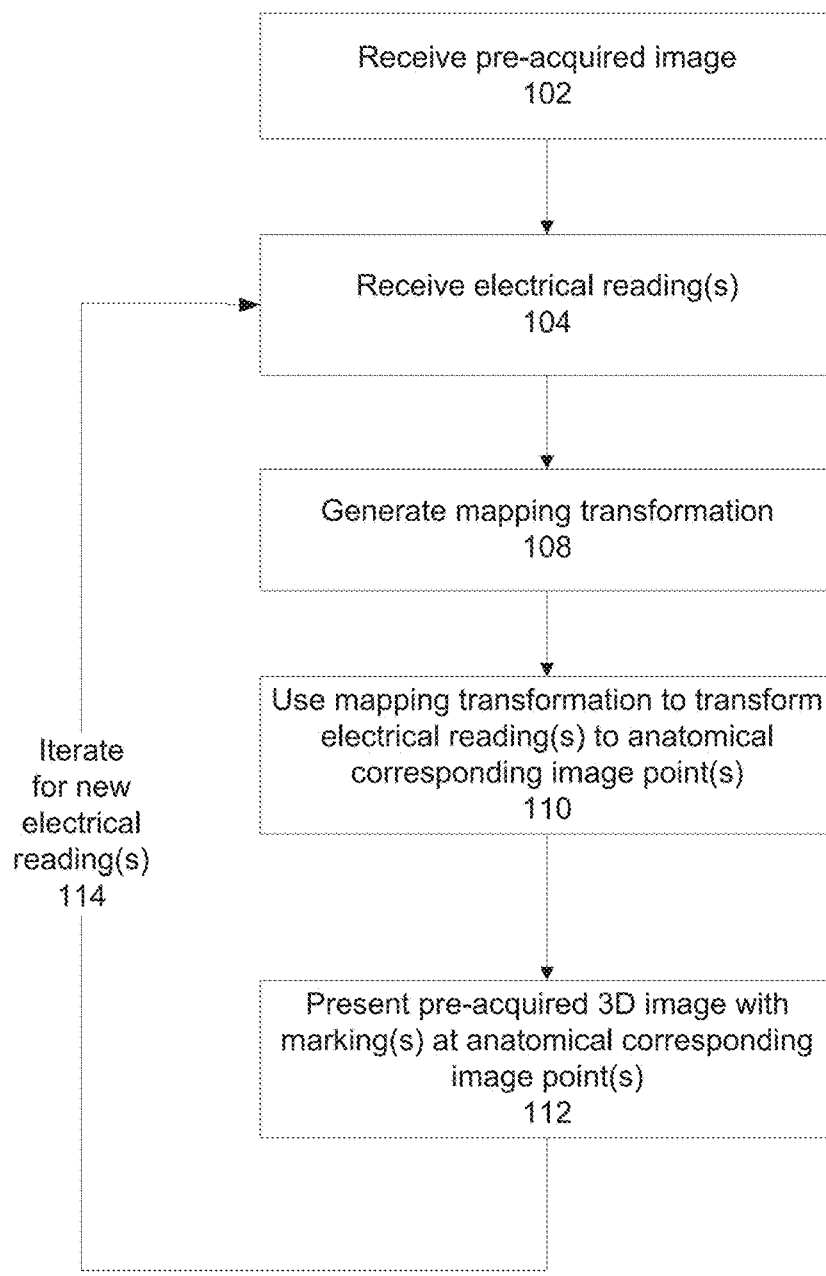
FIG. 1 is a flowchart of a method for transforming one or more electrical readings to anatomical corresponding image point(s) on a pre-acquired 3D image, in accordance with some embodiments of the present invention.

The present invention, in some embodiments thereof, relates to image registration and, more specifically, but not exclusively, to systems and methods for registration of electrical readings obtained from an intra-body location with a pre-acquired three dimensional image including the intra-body location. The electrical readings may include, for example, readings of voltage differences between inter-body electrodes and external electrodes, attached to the surface of the patient body at known places. The latter may also be known and sometimes referred to herein as patches or patch electrodes or pad-electrodes or pads. In some embodiments, electrical readings comprise the impedance between the inter-body electrodes and the patch electrodes. In some embodiments, the impedance between the inter-body electrodes and the patch electrodes is measured and used for the image registration. In some embodiments, the impedance is calculated based on the voltage difference. In some embodiments, electrical readings comprise a dielectric property measured by the inter-body electrodes.

An aspect of some embodiments of the present invention relates to systems and/or methods (e.g. code instructions executed by one or more processors) that receive one or more electrical readings obtained by inter-body electrodes associated with a catheter located within an intra-body portion (optionally a dynamic intra-body portion of a moving organ, for example, the heart), and transform the electrical reading(s) to anatomically corresponding image point(s) on a pre-acquired 3D image using a mapping transformation. The anatomically corresponding image point(s) represent anatomically correct mapping between the anatomical location of the inter-body electrodes generating the electrical readings and the corresponding anatomical location on the pre-acquired 3D image. The electrical readings are correctly transformed to the pre-acquired 3D image, even as the anatomy of the intra-body portion changes from when the pre-acquired image is obtained to the current state, for example, the dimensions and/or shape of the organ changes.

It is noted that the pre-acquired image may be obtained a period of time before the electrical readings are obtained, for example, several weeks, during which the dimension and/or shape of the organ changes.

The term intra-body portion may sometimes be interchange with the term organ.

It is noted that the heart is used herein as an exemplary organ, and is not necessarily limiting. The systems, methods, apparatus, and/or code instructions (stored on a data storage device executed by one or more processors) described herein may be applied to other organs within the body, optionally organs that include one or more lumens (e.g., chambers, cavities), optionally fluid filled chambers (e.g., with air, blood, urine, amniotic fluid, cerebrospinal fluid), optionally dynamic organs that move, change position, and/or change volume (e.g., expand, contract, rotate) for example, the heart, blood vessels, the esophagus, and/or urinary bladder.

The pre-acquired 3D image may also be referred to herein as the 3D image.

Exemplary states that change the anatomy (e.g., dimension, shape) of the intra-body portion (i.e., organ, for example, heart) include:

Patient postural changes, for example, placing a pillow under the shoulders of the patient, moving the hand of the patient, and rotating the patient. Movement of the patient changes the position of the internal organs, for example, the heart's position relative to the skin.

Hydration changes that lead to changes in the volume of organs with fluid filled lumens, for example, the heart. Hydration changes may occur, for example, due to hydration state of the patient, and/or drugs that change the amount of fluid in the body.

Cardiac cycle, during which the heart and/or arteries experience volume changes.

Medication use, for example, which may lead to changes in the operation of the organ (and therefore a change in effective dimension and/or shape).

The anatomically corresponding image point(s) may represent an anatomical location within the body of the patient, for example, a location on a wall within an inner chamber of the heart, for example, represented as a pixel, a set of pixels, a voxel, a set of voxels, or other representations. The anatomically corresponding image point(s) may correlate to the same location as the tissue moves, for example, as the heart wall expands and contracts due to hydration changes (and/or during the cardiac cycle), the location on the wall remains within the same anatomical location, for example, conceptually similar to inserting a pin within the anatomical location that remains pinned to the tissue throughout the cardiac cycle and/or volume changes due to hydration status.

The anatomically corresponding image point(s) may represent clinically relevant targets for which precision is important to accurately hit the target instead of nearby structures, for example, a ganglionated plexus or an atrial fibrillation rotor. The anatomically corresponding image point(s) correlate to the same location when there is an anatomical difference in the patient between when the pre-acquired image was captured and the real-time status of the patient when the electrical readings are captured, for example, the volume status of the patient may be different, for example, the patient may be hypervolemic or hypovolemic in real-time relative to the time of image capture. The volume changes may cause a difference in volume and/or shape of the heart ventricles. The systems and/or methods described herein correctly map the real time location of the electrode(s) of the catheter in the patient to the corresponding anatomical location(s) in the patient during capture of the pre-acquired image.

Optionally, the pre-acquired 3D anatomical image is corrected based on the electrical readings. The electrical readings may be used to transform the pre-acquired 3D anatomical image to correspond to the actual current anatomy of the patient. For example, the pre-acquired 3D anatomical image is transformed using a transformation function and/or map according to the electrical readings.

The anatomically corresponding image point(s) on the pre-acquired 3D image is maintained during dynamical motion of the intra-body portion, for example, while the heart is beating, while the patient is breathing, while the patient is changing positions (e.g., raising hands), and/or during blood volume changes (e.g., patient is administered fluid). For example, when the electrodes(s) of the catheter is contacting a certain region within the left atrium of the heart, and the left atrium is dynamically dilated (e.g., due to administration of a significant volume of saline), the anatomically corresponding image point(s) on the pre-acquired 3D image is maintained at the same certain region within the dilated left atrium that corresponds to the same certain region within the pre-dilated left atrium. For example, the certain regions may differ from each other by elasticity. For example, in some embodiments three (or four) regions may be defined: the appendage, anterior wall and posterior wall (considered as one or two regions), and mitral plane. Of these, the appendage is most elastic, the mitral plane is least elastic, and the anterior and posterior walls are of intermediate elasticities. In some embodiments, the image point(s) on the pre-acquired 3D image after the dilation or other change is in a region having certain degree of elasticity, and after the dilation or change, remains in a region having similar degree of elasticity (within a defined elasticity tolerance).

In some embodiments, marking of the image points may indicate the catheter position within the patient organ on the pre-acquired 3D image; e.g., to a physician during a medical procedure.

The systems and/or methods described herein maintain the relative location of the electrode(s) on the catheter to the anatomy of the organ, even as the location of the electrode(s) of the catheter relative to an external reference system changes. The anatomical correspondence is achieved based on the topology of the electrical readings from the electrode(s) of the catheter and the topology of anatomy obtained from the pre-acquired anatomical images (e.g., CT imaging). For example, when the catheter is located in the left atrium, topological correspondence is computed between the electrical readings of the electrode(s) of the catheter and the anatomical image(s) of the left atrium. The systems and/or methods described herein are based on relations between anatomical corresponding image points and electrical readings, without necessarily referring to static defined locations (e.g., manual markers) and/or without necessarily referring to data external to the points, for example, a static external coordinate system such as an inertial coordinate system, and/or the position of landmark points manually defined at the beginning of the procedure.

Optionally, the electrical readings are made by multiple electrodes located on the catheter, with known distances between the electrodes. Optionally, in such cases, the transformation of multiple electrical readings to corresponding anatomical image points on the 3D pre-acquired image is based on the pre-defined known distances between each of the multiple electrical readings (e.g., distances between the electrodes location on the catheter). The pre-defined distances can be used to set boundary conditions on the correspondence between the electrical readings and the anatomical corresponding image points on the 3D pre-acquired image. The distances are optionally used as a fixed limiting anchor during the transformation, while providing for non-rigidity of other parameters of the transformation.

Optionally, a new mapping transformation is generated for a new received electrical reading(s). The new electrical reading(s) are transformed to new anatomically corresponding image point(s) on the pre-acquired 3D image using the new mapping transformation. The new mapping transformation may be dynamically generated, in real-time, during navigation of the catheter within the heart and/or a treatment session. The new mapping transformation follows changes in the heart morphology, and maintains the correct anatomical correspondence between the actual location of the catheter within the body and the anatomical corresponding image point(s) on the 3D pre-acquired image.

Optionally, a correspondence is defined between image point(s) on the 3D pre-acquired image and electrical readings, so that the anatomical location within the body organ where the catheter is located when taking the readings anatomically correspond to the image points. The mapping transformation is optionally calculated by first determining the correspondence from the electrical readings to the pre-acquired image, and then by calculating a transformation.

The transformation (which may sometimes also be referred to herein as: mapping transformation, mapping transform, transformation function, transformation code, and transform) may be from the electrical readings to the pre-acquired image, or from the pre-acquired image to the electrical readings. In some embodiments, a first correspondence is used to find a first transformation, and the first transformation is used to define a second correspondence, which may be used for finding a second transformation, and so on until convergence of the transformations is achieved. In some embodiments, all the transformations in the iteration process are at the same direction (e.g., from electrical readings to anatomical locations). In some embodiments, the transformation may be at a different direction at each iteration. In some embodiments, a correspondence may be defined from image points to electrical readings, in one or more of the iteration. The process optionally ends where there is a converged transformation from electrical readings to image points. The generated mapping transformation may be used for mapping between electrical readings and anatomical corresponding image points in general, whether the readings were used for generating the transformation, or not. For example, a transformation may be generated based on a first set of readings, and used for transforming a reading not included in the first set.

Optionally, breathing movements of the patients are monitored, and used to correct the electrical readings which are transformed to the anatomical corresponding image point(s) on the 3D pre-acquired image. The electrical readings obtained by the catheter within the patient are optionally normalized according to the potential difference between two (or more) of the pad-electrodes to obtain normalized electrical readings. The transformation to the anatomical corresponding image point(s) is optionally performed based on the normalized electrical readings.

Optionally, static electrical readings from a statically positioned catheter located in a predefined organ-region (e.g., a location the physician may correctly identify based on experience and/or knowledge), for example in the coronary sinus, are used to obtain initial readings from a set of anatomically correct (or at least anatomically well defined) points on the 3D image. For example, the operator knows the catheter is in the coronary sinus (CS), and the CS is clearly identified in the pre-acquired image, so there is a correspondence between readings and electrode positions in the image that may be obtained even before the mapping begins, for example, if a catheter is introduced into the CS before the mapping begins. This correspondence may be used to define an initial transformation between readings and image points. While this transformation may be accurate only in the vicinity of the predefined organ-region (e.g., CS), it may be a reasonable starting point for searching for a transformation that would reasonably satisfy all the requirements (e.g., the coherence requirement and the distances between the electrodes) over the entire image. Thus, the dynamically obtained electrical readings (from another catheter being navigated within the body located within another organ-region) are transformed to the 3D image using the initial transformation of the static electrical readings. A mapping function is generated to map electrical readings from multiple electrodes within a static catheter positioned within a known organ-region within the patient, for example, within the coronary sinus of the heart. The coronary sinus may be used as a stable known reference. The mapping function maps the statically obtained electrical readings to corresponding anatomical image points on the pre-acquired 3D image within the coronary sinus. The mapping function is used to generate the mapping transformation that transforms an electrical reading of the catheter from inside a second organ-region of the patient to an anatomically corresponding image point in the 3D image. The second organ-region may be a region within the same organ as the known organ-region, for example, the known organ-region is the CS and the second organ-region is a chamber of the heart (e.g., LA, LV, RA, RV). Alternatively, the second organ-region may be a region within another organ, for example, the known organ-region is the CS and the second organ-region is a nearby structure external to the heart, for example, the inferior vena cava.

Alterations in the electrical readings in the static position (e.g., within the known organ-region, optionally the coronary sinus) over a significantly long period of time (e.g., at least 1 minute, or at least 5 minutes, or at least 10 minutes, or at least 30 minutes, or other periods of time) may be used to update the transformation of the electrical readings to the static anatomical location. The alterations may represent movement of the patient, for example, due to moving the patient's hand by the anesthesiologist, due to a cough of the patient, or due to a reaction of the patient to an anti-fibrillation electrical shock (e.g., electrical defibrillation or cardioversion). These alterations may be taken into account, for example, by comparing electrical readings before and after the movement, and generating a correspondence between the two sets of readings. In some embodiments, the alterations over time may be caused by gradual movement of the patch electrodes during the treatment. This may be accounted for by using newly measured values for updating a transformation function, transforming electrical readings to anatomically corresponding image points, e.g., as described herein.

In some embodiments, the alterations over time may be of high rate, and occur at a rate of, for example, about once per second or once per half second, or once per 2 seconds, or other rates. For example, the alterations may occur because of heart-beating and/or breathing. These movements may be associated with different changes in the electrical readings obtained by electrodes at different regions of the heart. For example, different regions move at different directions and to different extents at different portions of a heart beat and/or of a breathing cycle. Such known correlations between movements and positions in the heart may be used as anatomical location indicators that may be taken into consideration in generating the transformation function. In some embodiments, following these fast alterations may require a refresh rate of about 20 to 30 Hertz (Hz) per frequency. For example, if voltage differences are measured at two different frequencies, refresh rate of about 40 to 60 Hz may be effective for following these alterations in the electrical readings. In some embodiments, a refresh rate of 100 Hz is used.

Optionally, a graphical overlay is presented at a pre-defined anatomical location on the pre-acquired image. The graphical overlay may represent an optimal treatment zone, for example, a target for treatment using electrode(s) on the catheter (e.g., a point, line, or region targeted for ablation). The graphical overlay may be positioned on the pre-acquired image according to the anatomical corresponding image point(s). The graphical overlay may be morphed to fit the actual current anatomical state of the portion of the organ (e.g., heart) using the anatomical corresponding points as reference. The current position of the electrode(s) on the catheter may be presented relative to the graphical overlay, for example, to help position the ablation electrode(s) relative to the target tissue based on the graphical overlay. Moving the physical catheter within the anatomy of the patient adjusts the position of the ablation electrode(s) relative to the graphical overlay, for example, as part of the process of targeting tissue for ablation.

The systems and/or methods (e.g., code instructions executed by one or more processors) described herein address the technical problem of mapping the real-time, actual physical location of a catheter located within the body of a patient (e.g., within the heart, within a chamber of the heart, within the vasculature) to a corresponding anatomically correct point(s) on a pre-acquired image (e.g., a three dimensional image). In particular, the technical problem relates to correctly mapping the actual physical location of the catheter to the pre-acquired image during motion of the organ, for example, beating of the heart, and/or patient respiratory related movements. High accuracy of the actual location of the catheter within the body of the patient improves treatments using the catheter, for example, by helping the operator deliver treatment to a certain anatomical location more accurately.

The registration described herein may be performed relative to the pads (e.g., positioned on the skin of the patient), for example, in comparison to other registration methods which use inertial coordinates, in which the indication of catheter presented on the image moves as the catheter moves in respect to the room, even if the catheter is static in respect of the moving organ, the indication of the catheter may appear, according to some embodiments of the present invention, physically still on the screen.

Some conventional registration methods rely on manual user input for marking the correspondence between locations on the image and the body (e.g., by physically touching the body of the patient and the corresponding location on the image). This manual user input is used to generate the mapping between the image and the readings from the catheter. However, such mappings remain constant, and cannot adapt to changes and/or movement in the body that may occur during navigation, for example, volume changes in the heart due to hydration changes. In contrast, using the systems and/or methods described herein, the location of the indication of the catheter relative to the anatomy of the heart remains fixed, even as the heart changes size or location (e.g., due to increased hydration fluid or decreased hydration fluid, due to patient postural changes, and/or due to the cardiac cycle). For example, the indication of the catheter may appear static on the display as the heart increases or decreases in volume, since the indication of the catheter remains fixed relative to the same anatomical location.

The systems and/or methods described herein automatically register, during the procedure, positions within a lumen of an organ (e.g., chambers and/or vessels of the heart) that have been identified on a 3D and/or 4D image taken before the procedure began. The registration is performed with precision that is good enough to provide for targeting positions during the procedure. For example, in comparison to existing methods that rely on manual registration of pre-acquired images and result in poor precision that leads to inaccurate targeting. For example, the precision provided by embodiments of the current invention may be better than ±10 mm, without requiring any manual registration, while current methods that do require manual registration obtain accuracies of about ±20 mm with users that are regularly trained to provide manual registration, and up to ±7 mm with users that are highly trained to provide manual registration, and provided the manual registration is allowed about 20 to 30 minutes (to manually register 13-20 point pairs). In some embodiments of the present invention, these 20 to 30 minutes may be replaced by about 2 minutes of data collection and less than one minute of computation, even without employing a trained user.

It is noted that other registration methods that map electrical readings to pre-acquired anatomical images of the body of the patient are unable to perform correctly (e.g., within a predefined tolerance requirement) in cases of movement, since such methods are designed for registration of still images. The systems and/or methods described herein (e.g., the transformation code instructions, i.e., code instructions, that when executed by one or more processors carry out a transformation of one or more of the embodiments disclosed herein) are able to maintain anatomical correspondence of the electrical readings to image point(s) on the pre-acquired image, accounting for the movements of the organ, such as beating heart, breathing effects, patient movements, and changes in fluid volume of the patient.

The systems and/or methods (e.g., code instructions executed by one or more processors) described herein improve an underlying technical process within the technical field of image processing and/or image registration. The systems and/or methods described herein improve the process of mapping the location of electrode(s) located on a catheter (positioned within the body), to anatomically corresponding image point(s) on a pre-acquired image, which may be a pre-acquired 3D image, while the organ and/or tissues (from the body portion where the catheter is located) are moving.

The systems and/or methods described herein (e.g., code instructions executed by one or more processors) improve performance of the computing device executing the transformation code (that transforms the electrical reading(s) to the anatomically corresponding image point(s)) and/or other code instructions described herein (e.g., code instructions that dynamically generate a new transformation function). The improvement in performance is obtained by reducing the processing time, processing resources, and/or memory resources to compute the transformation, and/or compute the transformation function (e.g., transformation code), to achieve the anatomically correct transformation described herein. For example, manual markings between the actual location of the catheter within the body and the corresponding location on the image may be reduced or prevented. In another example, fluoroscopic time to obtain real-time x-ray images of the catheter within the body (which are registered to the pre-acquired 3D image) is reduced or omitted, since the registration to the pre-acquired 3D image is accurately and/or correctly performed using the electrical readings.

The systems and/or methods described herein (e.g., code instructions executed by one or more processors) are tied to physical real-life components, for example, using electrical readings obtained from a physical electrode located on a catheter. The computed anatomical corresponding image point(s) is presented on the pre-acquired image on a physical display.

The systems and/or methods described herein provide a unique, particular, and advanced technique of mapping electrical readings obtained from inside the body of a patient (e.g., using one or more electrodes located on a catheter) to anatomical corresponding point(s) on a pre-acquired 3D image.

Accordingly, the systems and/or methods described herein are inextricably tied to computer technology, to overcome an actual technical problem arising in image processing, in particular image registration, to help a user more accurately navigate a catheter within the body of a patient (e.g., within the heart) and/or help a user more accurately use the catheter to perform a treatment within the body of the patient.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s).

In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term 3D image, or image, may sometimes be interchanged with one or more 2D images, or with a 4D image, or other representations.

As used herein, the term mapping and transformation may sometimes be interchanged, for example, with reference to mapping and/or transforming electrical reading(s) to the anatomical corresponding image point(s) on the pre-acquired image.

As used herein, the term point with reference to the anatomical corresponding image point on the pre-acquired image means a pixel, a voxel, a set of pixels, a set of voxels, or other logical and/or physical unit used for logical representation and/or physical presentation of the pre-acquired image.

As used herein, the use of the term heart is not meant to be necessarily limiting. The term heart is meant as an example of an organ and/or tissue (and/or a portion thereof) that moves and/or changes shape while a catheter is navigating in it, for example, pulsation of arteries (due to the cardiac cycle), peristalsis of the colon and/or other portions of the intestine, movement due to breathing, and movement due to the cardiac cycle. Other exemplary organs include: blood vessels, bladder, brain ventricles, uterus, colon, and stomach.

As used herein, the term move or movement of an organ (or portion of the organ) does not necessarily require change of the position of the center of mass, but may include displacement of the position of the center of mass. Examples of movement that do not necessarily include displacement of the position of the center of mass include, for example, movement due to muscle contraction and relaxation cycles, volume change, peristalsis, and/or rotation along a central axis, which may effectively remain at an approximate center of mass.

Figure 2:
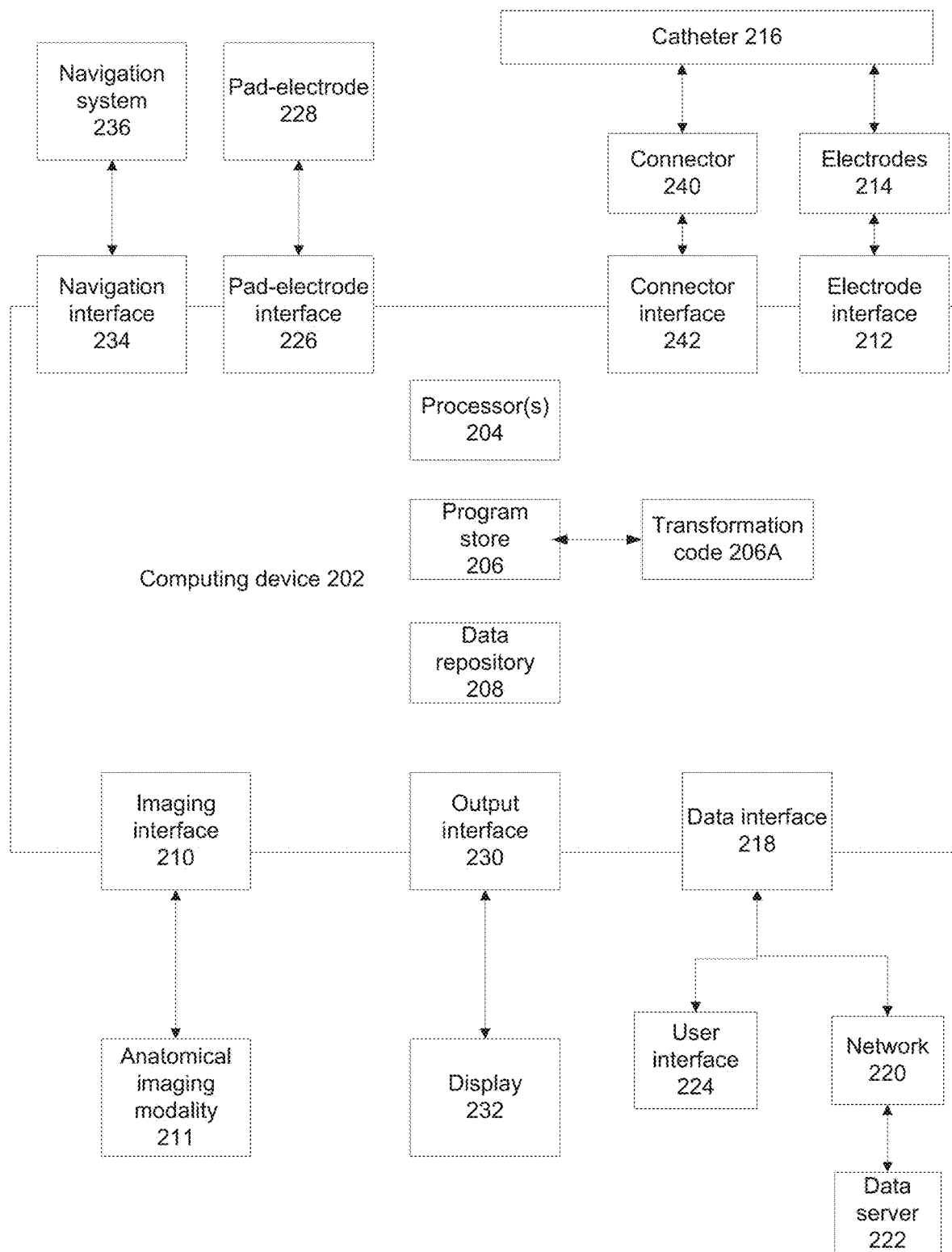
FIG. 2 is a block diagram of components of a system that maps electrical readings to anatomical corresponding image point(s) on a pre-acquired 3D image, in accordance with some embodiments of the present invention.

Reference is now made to FIG. 1, which is a flowchart of a method for transforming one or more electrical readings (from respective electrodes mounted on a catheter inside an organ or portion thereof, for example, a portion of the heart) to anatomical corresponding image point(s) on a pre-acquired 3D image of the organ or the portion thereof, in accordance with some embodiments of the present invention. Reference is also made to FIG. 2, which is a block diagram of components of a system 200 that maps electrical readings to anatomical corresponding image point(s) on a pre-acquired 3D image, in accordance with some embodiments of the present invention. The method described with reference to FIG. 1 and/or system 200 described with reference to FIG. 2 present (on a display, and/or store for presentation, and/or transmit to another computing device for presentation) the pre-acquired 3D image with an accurate representation of the location of the catheter within the heart, which may be used by an operator to more accurate navigate within the heart, and/or more accurately perform procedures and/or treatments within the heart, for example, ablation (e.g., radiofrequency ablation), injection, and/or puncture.

Figure 3:
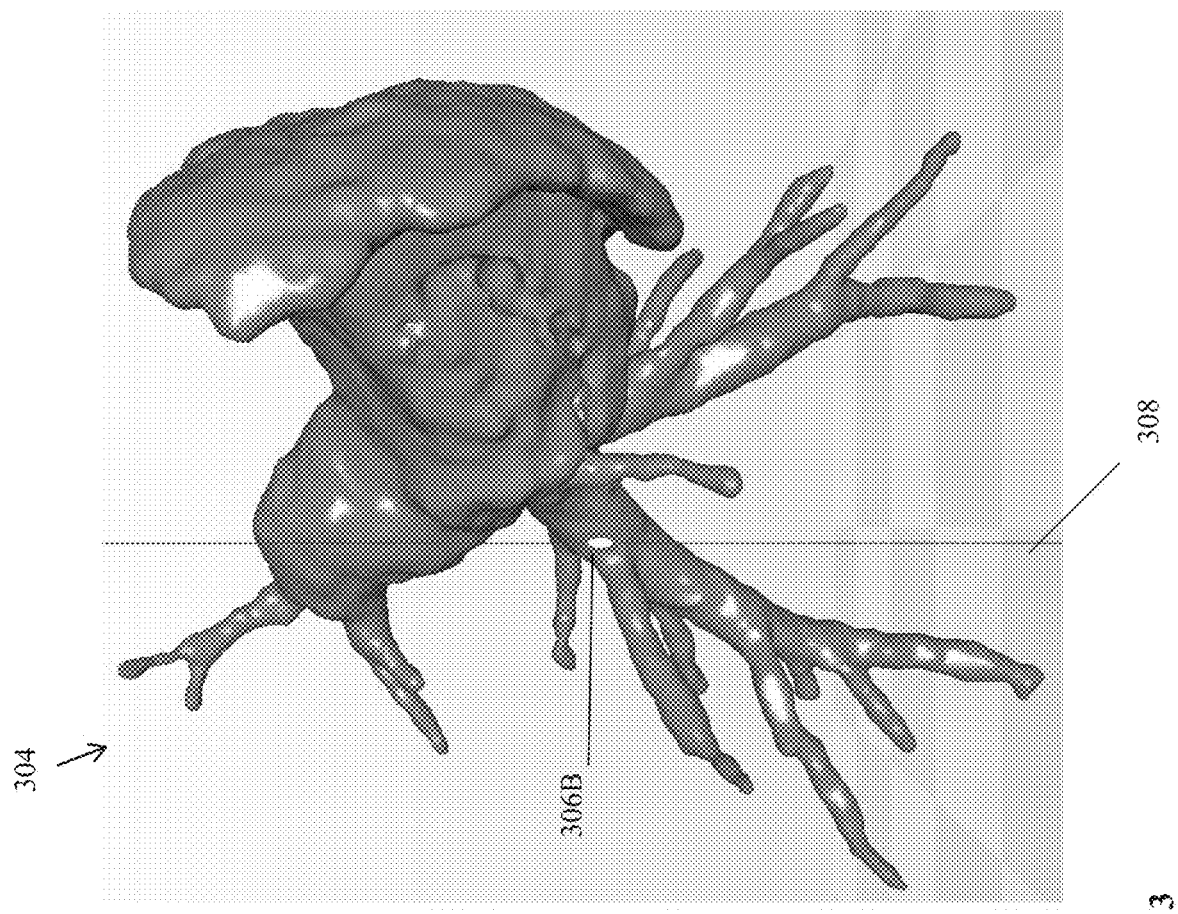
FIG. 3 is includes two CT images of a left atrium (and pulmonary arteries) at two different motion states, to help illustrate the anatomical correspondence property described herein, in accordance with some embodiments of the present invention.
Figure 3:
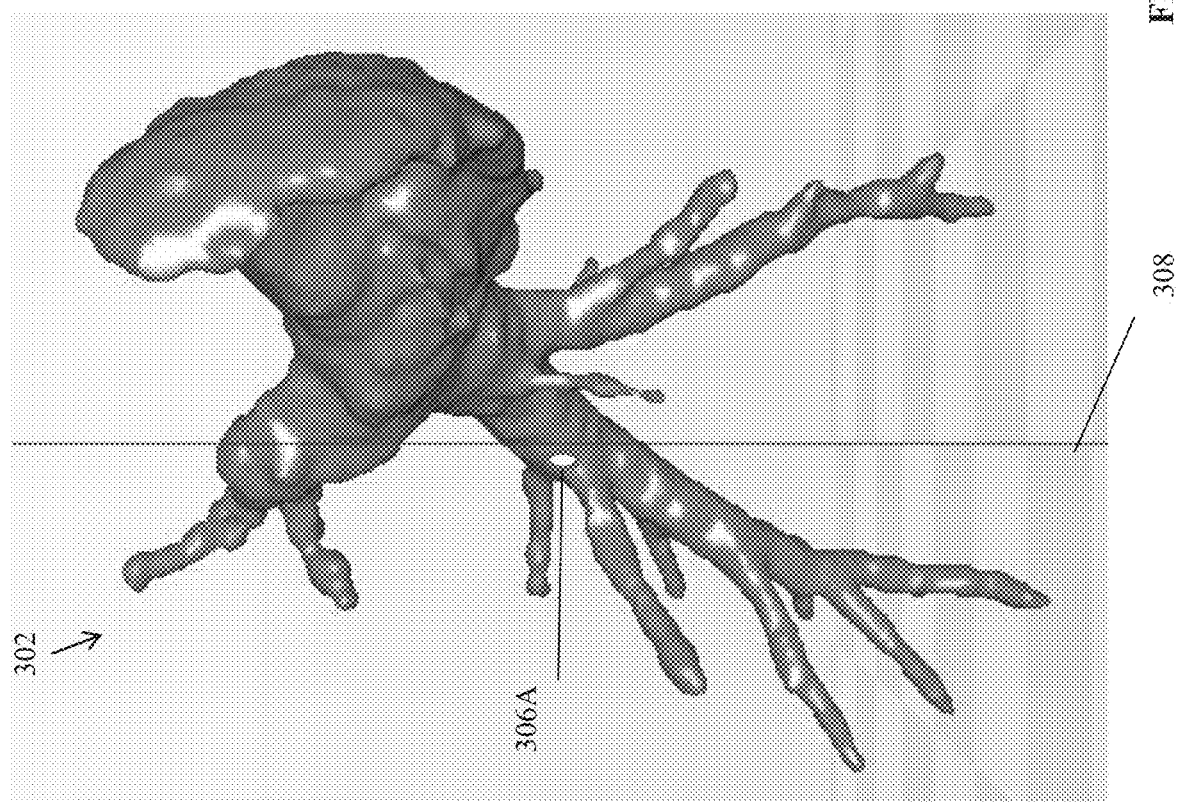

Reference is now made to FIG. 3, which includes two CT images of a left atrium (and pulmonary arteries) at two different motion states, to help understand the anatomical correspondence property of the systems and/or methods (e.g., transformation code instructions executable by one or more processors) described herein, in accordance with some embodiments of the present invention.

Image 302 represents a first state of the left atrium. Image 304 represents a second state of the left atrium, in which the left atrium moved relative to image 302. In particular image 302 depicts the left atrium in systole which includes the minimum volume after contraction, and image 304 depicts the left atrium in diastole which includes the maximum volume during filling, before the contraction. Alternatively, the first state may represent the state of the patient during acquisition of the 3D image (e.g., dehydrated) and the second state may represent the state of the patient during the procedure (e.g., hydrated by bolus intravenous infusion of saline).

Points 306A and 306B are an example of anatomically corresponding image point(s) on a pre-acquired 3D image, as described herein. Points 306A and 306B are two different points, each located on a different respective image 302 and 304. However, points 306A and 306B correspond to each other anatomically, relating to the same anatomical position of the heart.

Point 306A represents an arbitrary location in the heart. Point 306B is shown on an expanded heart, and represents a point that anatomically corresponds to point 306A. It is noted that points 306A and 306B have different coordinates in a static external coordinate system, such as, for example, the bed coordinate system or the camera coordinate system. The different locations in respect to the static external coordinate system are illustrated in the figure by the different distances of the points from line 308 which is static and external to the heart. Conceptually, image points 306A and 306B may represent the location of a pin inserted into the pulmonary artery. The anatomical location of the pin remains constant throughout the cardiac cycle, as the left atrium expands and contracts and moves, even though the location of the pin in relation to a static external coordinate system has moved.

Line 308 represents an arbitrary external reference, for example, used by other methods, to determine the location of the catheter based on electrical readings obtained by the electrode on the distal end of the catheter. Since the external arbitrary reference is fixed, line 308 is stationary, and the heart as depicted by images 302 and 304 appears to move relative to line 308. Moreover, it is noted that although anatomically points 306A and 306B are both images of the same anatomical point within the pulmonary artery, they appear in the two images in different locations relative to line 308. Thus, if each of the images were registered with a third image (not shown) according to embodiments of the present invention, point 306A and point 306B would register to the same point in the third image, whereas in contrast when other methods that are based on an arbitrary external reference are used points 306A and 306B would incorrectly register to different points in the third image.

In another example, the user may use a user interface (e.g., GUI) to mark image point 306A on image 302 (during the first state), and when the image is updated to image 304, his marking will appear at image point 306B. When the user navigates the catheter to the physical location within the pulmonary artery of the patient corresponding to image point 306A and/or 306B, the actual location of the catheter is correctly determined by correlating the electrical readings obtained by the electrode(s) on the distal end of the catheter to the marked image point 306A-B within a tolerance, for example, about 3 mm, or about 1 mm, or other values. The catheter is navigated to the correct location (corresponding to image point 306A-B) even when the heart is beating, and/or even when the anatomical configuration of the heart changed from when the image was acquired (e.g., due to dehydration, hydration, and patient movement).

Referring now back to FIG. 2, system 200 may include a computing device 202 that includes a program store 206 storing code (as described herein) and a processor 204 coupled to program store 206 for implementing the stored code. Optionally, more than one processor may be used. It is noted that program store 206 may be located locally and/or remotely (e.g., at a remote server and/or computing cloud), with code optionally downloaded from the remote location to the local location for local execution (or code may be entirely or partially executed remotely). Program store 206 may store transformation code 206A that includes code instructions to generate the transformation function described herein, and/or compute the transformation of the electrical reading(s) to corresponding anatomical image point(s) on the pre-acquired 3D image, e.g., by executing the transformation generated, as described herein.

Processor(s) 204 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 204 may include one or more processors (homogenous or heterogeneous), which may be arranged for parallel processing, as clusters and/or as one or more multi core processors.

Program store 206 stores code instructions implementable by processor(s) 204. Program store 206 may be for example, a random access memory (RAM), read-only memory (ROM), and/or a storage device, for example, non-volatile memory, magnetic media, semiconductor memory devices, hard drive, removable storage, and optical media (e.g., DVD, CD-ROM).

Computing device 202 may include an imaging interface 210 for communicating with one or more anatomical imaging modalities 211 that acquire a dataset of imaging data of a patient (referred to here as the pre-acquired 3D image). Examples of anatomical imaging modalities include computer tomography (CT) machine, an ultrasound machine (US), a nuclear magnetic resonance (NM) machine, a single photon emission computed tomography (SPECT) machine, a magnetic resonance imaging (MRI) machine, and/or other structural and/or functional anatomical imaging modality machines. Optionally, imaging modality 211 acquires three dimensional (3D) image data and/or 2D data and/or 4D data. It is noted that the anatomical images may be derived and/or acquired from functional images, for example, from functional images from an NM machine. In some embodiments, the connection between imaging modality 211 and the computing device 202 may be via data transfer. For example, image data from the imaging modality may be downloaded to a portable memory device (e.g., disk on key), and interface 210 may be a disk-on-key socket, allowing to upload the image data, for example, to data repository 208.

Computing device 202 may include an output interface 230 for communicating with a display 232, for example, a screen or a touch screen. Optionally, the transformed electrical readings are displayed within a presentation of the pre-acquired 3D image, for example, the 3D pre-acquired image is displayed on display 232, with a marking indicating on the displayed image the location of the distal end of the catheter within the heart based on the transformation. Additionally or alternatively, a distinct color (e.g., yellow, bright green) marking on the pre-acquired 3D image may indicate a predefined anatomical location, e.g., a region to be treated. The relation between the markings of the predefined anatomical location and the real-time location of the distal end of the catheter may attain anatomical significance and accuracy, so that a physician looking at the display can navigate the catheter to the region to be treated at a predetermined accuracy, which in some embodiments may be better than 10 millimeters (mm), better than 5 mm, or even better than 2 mm.

Computing device 202 may include an electrode interface 212 for communicating with a plurality of physical electrodes 214 located on a distal end portion of a physical catheter 216 designed for intra-body navigation, for example, an electrophysiology (EP) ablation catheter, and/or other ablation catheter (e.g., chemical ablation or injection catheter). Catheter may be Lasso® catheter by Biosense Webster. In some embodiments, catheter may include 2-20 electrodes; e.g., 4 electrodes. Catheter may include multiple electrodes (e.g., four electrodes) arranged on a straight, non-deflectable line. Optionally, catheter may include a single tip electrode and three ring electrodes. Alternatively or additionally, system 200 includes a navigation interface 234 for communicating with a catheter navigation system 236, optionally a non-fluoroscopic navigation system, optionally, an impedance measurement based system.

Exemplary types of catheters 216 include: steerable, Lasso (a trademark of Biosense), non-irrigated, and irrigated.

Exemplary electrode 214 configuration of catheter 216 include: 4 electrode ablation catheters with 1 RF electrode, 4-10 electrode single line diagnostic catheter (e.g., His, Decapole, Lasso, and the like), phase RF (i.e., RF issued from multiple electrodes), microelectrodes, basket, Penta Ray, and 20 electrode diagnostic.

Reference is now made to FIG. 5, which includes a list of exemplary catheters 216, in accordance with some embodiments of the invention.

Referring now back to FIG. 2, catheter 216 may include one or more contact sensors for determining contact between the respective contact sensor and the organ (e.g., the inner wall of the lumen within which catheter 216 is located). The contract sensors may be implemented as dedicated contract sensors (e.g., that measure contract based on force) and/or electrode(s) 214 may serve a contact sensor function (e.g., contact may be determined by a change in certain impedance, voltage, and/or other electrical reading).

In one example, the electrodes perform the ablation, and sense the electrical field and/or impedance of tissue (used for navigation).

Optionally, computing device 202 includes a pad-electrode interface 226 for communicating with one or more pad-electrodes 228, which are positioned externally to the body (e.g., on the skin of the patient), the electrical signals of which are used to estimate effects of motion of the body of the patient, such as due to respiration, as described herein, and/or generate electrical fields, the voltage they generate is measured by the electrodes and transformed to locations in the pre-acquired image.

Optionally, computing device 202 includes a data interface 218, for communicating with a data server 222, directly or over a network 220, for example, to obtain the pre-acquired image, provide the generated transformation function and/or anatomically corresponding image point(s) for storage and/or remote presentation.

Optionally, a user interface 224 is in communication with data interface 218, for example, a touch screen, a mouse, a keyboard, and/or a microphone with voice recognition software.

Optionally, computing device 202 includes a connector interface 242 that communicates with a connector 240 connecting to catheter 216 (e.g., RF ablation catheter, injection catheter). Connector 240 may be used, for example, to transmit control signals to catheter 216 to control a medical procedure, for example, control the RF ablation electrodes for an ablation procedure.

It is noted that one or more interfaces 210, 218, 212, 226, 230, 234, 242 may be implemented, for example, as a physical interface (e.g., cable interface), and/or as a virtual interface (e.g., application programming interface). The interfaces may each be implemented separately, or multiple (e.g., a group or all) interfaces may be implemented as a single interface.

Processor 204 may be coupled to one or more of program store 206, data repository 208, and interfaces 210, 218, 212, 226, 230, 234, 242.

Optionally, computing device 202 includes a data repository 208, for example, for storing the pre-acquired image, received electrical parameters, and/or other data (such as: health record of a patient). The data, wholly or partially, may be displayed to a user (e.g., physician) before, during and/or after the procedure. Data repository 208 may be implemented as, for example, a memory, a local hard-drive, a removable storage device, an optical disk, a storage device, and/or as a remote server and/or computing cloud (e.g., accessed using a network connection).

It is noted that computing device 202 may include one or more of the following components: processor(s) 204, program store 206, data repository 208, and interfaces 210, 218, 212, 226, 230, 234, 242, for example, as a stand-alone computer, as a hardware card (or chip) implemented within an existing computer (e.g., catheterization laboratory computer), and/or as a computer program product loaded within the existing computer.

At 102, computing device 202 receives data of a pre-acquired image of at least a portion of the patient including a target tissue, optionally the heart of the patient. Optionally, the 3D pre-acquired image is obtained by anatomical imaging modality 211, before the catheter based treatment procedure (i.e., prior to insertion of the catheter into the patient), for example, at least 24 hour, or at least 1 week, or at least 1 month, or at least 3 months prior to insertion of the catheter. Alternatively, the 3D pre-acquired image is obtained as part of the catheter based treatment procedure, optionally while the catheter is located within the patient, or a short period of time before the catheter is introduced (e.g., about 1 hour, or about 3 hours).

As used herein, the term (3D) pre-acquired image, or image (of the patient) means a set of data representing an anatomical image of the patient, acquired by an imaging modality, for example, a CT machine, an MRI machine, etc. The pre-acquired image may be a processed image, for example, to create an internal endoscopic view for navigation, or a 3D rendering of organs, or slices, or other image representations.

At 104, one or more electrical readings from electrode(s) 214 mounted on a catheter 216 (e.g., the distal portion thereof) inside the portion of the heart (or other location inside the body) of the patient are received. The electrical readings may be received and/or processed by computing device 202. Catheter 216 is navigated within the vasculature of the patient by the operator.

The electrical reading(s) include, for example, electrical voltage, electrical currents, and/or electrical impedance. It is noted that under the assumption of a constant current, differences in voltage may be translated to differences in impedance. Impedance is not necessarily measured directly and absolutely.

Optionally, the received electrical reading(s) includes a reading of electrical impedance and/or another dielectric property. A dielectric property includes certain measured and/or inferred electrical properties of a material relating to the material's dielectric permittivity. Such electrical properties optionally include, for example, conductivity, impedance, resistivity, capacitance, inductance, and/or relative permittivity. Optionally, dielectric properties of a material are measured and/or inferred relative to the influence of the material on signals measured from electrical circuits. Optionally, a dielectric property of a material is measured and/or inferred relative to the influence of the material on an applied electric field. Measurements are optionally relative to one or more particular circuits, circuit components, frequencies and/or currents.

The electrical readings represent the position of electrode(s) 214 of catheter 216, optionally based on measured potential (e.g., voltage) relative to body surface electrodes (also referred to herein as patches or pad electrodes) located outside the body of the patient, for example, on the skin of the patient. Optionally a set of 3 pairs of patches are used, through which a low current in three distinct frequencies is applied. The 3 pairs of patches are positioned to correspond to three axes, X, Y, and Z. In some embodiments, the three axes are orthogonal to each other, but in some embodiments orthogonality is compromised, in favor of, e.g., comfortable attachment of the patches to the patient's skin.

The measured potentials difference, Vx, between one patch and an electrode inside the patient's body indicates the position of the electrode. Optionally, Vx, Vy, and Vz are each monotonic functions along their respective axis. It is noted that impedance may be used to indicate proximity to the inner blood vessel wall, and/or proximity to the pulmonary veins.

Optionally, multiple electrical readings are received, each from a different electrode mounted on the catheter. Optionally the electrical readings are performed simultaneously and/or are received simultaneously (e.g., within a tolerance requirement, which may represent an insignificant amount of time). The electrodes are mounted on the catheter at known distances from each other, for example, about 5 millimeters (mm) apart, or about 10 mm, or about 12 mm, or about 15 mm, or other distances.

The different electrodes mounted on the catheter are mounted along a longitudinal axis of the catheter at a distal, rigid, end region of the catheter. The electrodes are mounted along a rigid portion of the distal end region of the catheter.

For example, using an EP (electrophysiology) catheter having a single tip electrode and 3 ring electrodes, the tip electrode may be used, in addition to one or more of the ring electrodes. The fixed physical distance between each electrode is about 12 mm.

Optionally, breathing movement of the patient is monitored. The monitoring may be performed, for example, by measuring the electrical readings (e.g., set of voltage readings and/or voltage differences between the electrodes on the catheter and the externally applied pad-electrodes) over time corresponding to the breathing cycle, optionally when the catheter is not being maneuvered by the operator. Changes in the voltage potential may be determined to be due to the breathing movement. The electrical readings may be corrected according to the breathing movement to obtain a set of corrected electrical readings.

The corrected electrical reading may represent the location of the catheter without the effects of the breathing movement, which may be more accurately mapped to the pre-acquired image, to achieve more accurate anatomical correspondence (by removing the effects of the breathing). The transformation described herein may be performed using the corrected electrical readings. The electrical readings may be corrected by normalizing to a potential difference between two of the external pad-electrodes to obtain normalized electrical readings. The normalized electrical readings may be transformed by the mapping transformation.

The correction may be calculated by first analyzing the transformation from the pre-acquired image (e.g., still image) to the measured set of voltages (e.g., the electrical readings). The transformation (e.g., vector, matrix, function) from a point on the pre-acquired image to the corresponding voltage measurements (e.g., set of three dimensions) may be represented as Transform(Image_point)=Image_point+ DELTA1+DELTA2*breathing-phase, where DELTA1 is a constant vector (depending on the pre-acquired image point), DELTA2 is a smaller vector that describes changes with breathing-phase, and breathing-phase is the current state during the breathing cycle, which may be analyzed using one or more methods, for example, correlated with patient inhalation and/or exhalation measurements. Once the transformation from the image to the voltage electrical readings is known, the correction may be calculated by calculating the reverse transformation from the voltage electrical readings to the image. The transformation calculations may be performed iteratively, to reach a steady state transformation.

At 108, a mapping transformation that transforms each electrical reading of the catheter from inside the portion of the heart (or other organ or portion thereof) of the patient to an anatomically corresponding image point in the pre-acquired 3D image is generated. The mapping transformation may be represented, for example, as a mapping matrix, a set-of-rules, a set of values for predefined parameters, a script, code instructions (e.g., executable), or other implementations. The generated mapping transformation may be stored in data repository 208 and/or program store 206.

Optionally, the mapping transformation is generated using a non-rigid registration algorithm.

Optionally, the mapping transformation is created based on a modification of a coherence point drift (CPD) method, described with reference to Myronenko, Andriy, Xubo Song, and Miguel A. Carreira-Perpinán. "Non-rigid point set registration: Coherent point drift." *Advances in Neural Information Processing Systems*. 2006. One or more modification of the CPD method described herein may be used. The CPD method estimates the probabilistic correspondence between readings and locations in the pre-acquired image. In some embodiments, the mapping transform used for the registration is a CPD transform, modified so that the probability attributed to a certain correspondence between electrical readings and image points depends on the known distance between the electrodes on the catheter, in addition to the dependence of said probability on the coherence requirement of the conventional CPD.

Optionally, the mapping transform is computed according to a probability that a certain element of the pre-acquired image (e.g., pixel, voxel), corresponds to a certain electrical reading. Alternatively or additionally, the mapping transform is computed according to a probability that a certain electrical reading corresponds to a certain element of the pre-acquired image.

Optionally, the mapping transform is computed based on minimization of a cost function that denotes coherency between the electrical readings and points of the pre-acquired image, where the electrical readings are constraint according to the known distance between the electrodes.

Optionally, the mapping transformation is generated based on a probabilistic correspondence model that defines the correspondence between the electrical points and points of the pre-acquired image as a probability. The probabilistic correspondence model is optimized while respecting the known distances between the electrodes that acquired the electrical readings. The optimization may be performed based on quasi-neutral optimization methods.

It is noted that when local-scale restrictions are set (i.e., the known distances between electrodes of the catheter performing the electrical readings), the optimization method implemented for the CDP method (i.e., expectation-maximization) cannot be implemented. Other substantially different optimization methods are implemented, for example, quasi-neutral optimization methods, implemented based on the fixed known distances between electrodes performing the electrical readings.

Optionally, the mapping transformation is performed for a cloud of electrical readings. The operator may obtain readings from multiple different points within the heat, by exploring one or more target regions (e.g., the right atrium (RA)+the inferior and superior caval veins (IVC and SVC), or the left atrium (LA)+the four pulmonary veins (PVs)). By manually maneuvering the catheter and performing a fast anatomical mapping process, the cloud of potential triplets (Vx, Vy, Vz) is acquired. The cloud is compared by code instructions to the pre-acquired, optionally high resolution, 3D image of the target region, for example, the CT or MR image.

The comparison between the 3D image and the cloud reveals that the V cloud of electrical readings appears as a distortion of the anatomy, and may partially match the CT image. For examples, the PVs entering the LA may be seen in the V cloud image clearly, but their positions (e.g., one in respect to the other) may be distorted in comparison to what's shown in the pre-acquired image and/or in comparison to general knowledge about the anatomy in general. It is noted that the main reason for distortion is the inhomogeneity of the dielectric properties of different body tissues.

The generated mapping transformation assigns V point(s) (e.g., set of Vx, Vy, Vz measurements), also referred to herein as the V cloud and/or also referred to herein as the electrical readings, to anatomical corresponding point(s) on the pre-acquired image (e.g., CT image). The generated mapping transformation represents a registration between the electrical readings and the pre-acquired image. The generated mapping transformation may be a non-parametric algorithm (implemented as code instructions) that calculates a distortion field (e.g. transformation) from the V cloud to the pre-acquired image.

The operator may navigate and/or perform procedures in the heart using the pre-acquired image, guided by the electrical readings that are registered to the pre-acquired image using the generated mapping transformation. The use of real-time imaging (e.g., x-ray fluoroscopic images) to determine the location of the catheter may not necessarily be needed, and/or the use of such imaging may be reduced when the operators uses the pre-acquired image accompanied by indications based on the electrical readings for guidance. It is noted that the pre-acquired image allows the operator to navigate using different views of the anatomy, for example, an endoscopic view, in which the operator views the distal tip of the catheter within the blood vessels and/or heart chambers, with the blood removed, to allow visualization within the blood vessel and/or heart chamber (e.g., the inner walls of the chamber and/or blood vessel).

Optionally, the mapping transformation is dynamically created in real time during navigation of the catheter. In such a navigation phase, the operator is able to navigate the catheter based on the pre-acquired image. Alternatively or additionally, the mapping transformation is calculated during a pre-navigation phase, and/or optionally updated during the navigation phase. In the pre-navigation phase, an initial mapping transformation may be used to find the transformation between the electrical readings and the pre-acquired image.

In some embodiments, the pre-acquired image may be transformed so that the distance between two given electrodes is constant across the image. As discussed herein, the anatomy of the organ presented on the pre-acquired image may be different from the current anatomy of the organ when the electrical readings are being acquired, for example, volume changes due to hydration differences between when the pre-acquired image is obtained and the current state of the patient when the electrical readings are obtained. The organ on the pre-acquired image may not correctly correspond to the current state of the organ represented by the electrical readings. Assuming that the organ anatomy correspondence between the pre-acquired image and the current state for which electrical readings are obtained results in a distortion of the image of the catheter presented on the pre-acquired image, causing the catheter to appear differently at different parts of the heart. For example, the distance between two given electrodes may be different at different parts of the heart. In some embodiments, the pre-acquired image is transformed based on the known distance between the electrodes of the catheter, which is kept constant everywhere the catheter is moved within the organ. The transformation of the pre-acquired image corrects the anatomy of the organ appearing on the pre-acquired image according to the actual anatomy of the organ at the time during which the electrical readings are obtained.

Optionally, the transformation of the pre-acquired image includes portions of the organ external to the location from which the electrical readings are obtained. The external portions are transformed according to electrical readings obtained at a different location. For example, transformation of the entire image of the heart and/or parts external to the left ventricle (e.g., right atrium, right ventricle) are transformed based on electrical readings obtained from the left ventricle.

The transformation of the pre-acquired image may be performed, for example, based on a non-constant scaling derived from the mapping transformation, and then the image is transformed so that distances on the image are changed, and the scale becomes constant. Optionally, a back registration process is performed (e.g., based on an inverse of the transformation function), to verify the mapping between the image points on the transformed pre-acquired image back to the electrical readings. The transformation of the image may be an iterative process, for example, until a stop condition is met, for example, accuracy within an error threshold. This may result in a constant inter-electrode distance across the image, and thus help the operator in understanding intuitively the sizes of features shown in the image, by comparing it to the inter-electrode distance. Thus, in such embodiments, the pre-acquired image is modified based on the transformed electrical readings.

It is noted that the transformed pre-acquired image may undergo an additional transformation during the procedure, for example, a period of time into the procedure after the initial transformation of the pre-acquired image. The additional transformation may be performed, for example, to account for anatomical changes to the organ that occurred during the procedure, for example, change in hydration that occurred during the procedure and changed the anatomy of the heart.

The initial mapping transformation may be obtained, for example, based on a stored previously generated mapping transformation (for the current patient and/or other patients), based on an initial guess, based on a simulation of the electrical fields expected in the heart considering the pre-acquired image, and/or based on other method described herein (e.g., using a second catheter positioned within a defined organ-region, for example, within the coronary sinus). Once electrical readings are available, the initial mapping transformation is updated and/or corrected to dynamically compute the mapping transformation. The mapping transformation may be iteratively computed and/or updated as additional electrical readings are received. For example, a noise parameter may measure the level of accuracy of the dynamically computed mapping transformation, and/or may represent a stop condition for stopping the iterations for computation of the mapping transformation. The generated mapping transformation is used during navigation, to transform the electrical readings (e.g., set of V measurements) to the anatomical corresponding image point(s) on the pre-acquired image.

Optionally, contact between one or more electrodes and tissue of the wall of the blood vessel lumen and/or heart chamber lumen is identified based on the impedance (which may be calculated from the measured voltage). The mapping transformation may be generated to map wall point(s) in the heart chamber to anatomically corresponding wall point(s) in the pre-acquired 3D image. The measured impedance value (or conversion from voltage) is evaluated to determine whether the electrode is contacting tissue or contacting blood, for example, based on a set-of-rules, predefined ranges, a statistical classifier, or other methods. In the present description and claims, the term tissue does not use to cover blood as such.

For example, in reference to impedance measured inside the blood pool of a heart chamber, a relatively higher impedance value is measured when the electrode contacts the endocardial surface of the heart chamber, and a relatively higher impedance is measured when the electrode contracts the inner wall of the blood vessels that branch off the cardiac chambers (e.g., the pulmonary veins that drain into the left atrium). In some embodiments, the mapping transformation is generated based on the identification of the physical contact between the electrode and the tissue. For example, when the impedance value is indicative of the electrode contacting the wall of the left ventricle, but the transform of the voltage readings brings the electrode to be located a distance from the wall, the location of the electrode is corrected according to the impedance, to contact the wall. Optionally, the transform is also corrected so that points at the vicinity of the catheter tip are transformed to the vicinity of the wall.

Optionally, when the mapping transformation is calculated based on multiple electrodes having predefined known distances, the mapping transformation is calculated using the predefined distance(s) between electrodes as a constraint on the mapping transformation. Electrical readings that are measured simultaneously (e.g., using the front and back electrodes) are mapped to anatomical corresponding points in the pre-acquired image that are separated by the pre-defined distance. The constraint may be applied as a computed scale according to the relative size of the image. The distance constraint may be applied even in the case where the spaced apart electrode read different values, for example, due to dielectric effects of tissues, such as blood and muscle.

Alternatively or additionally, the mapping transformation (e.g., an initial transformation) is calculated using a set of simulation data associated with the pre-acquired 3D image. The simulation data may include electrical readings expected to be read from different points in the pre-acquired image. The simulation data may be based on dielectric parameters of the tissues. The simulation data may be calculated using simulation code instructions. For example, each tissue type (e.g., bone, fat, muscle, blood vessel) may be segmented from the image and assigned a characteristic dielectric coefficient value (e.g., from a dataset of values based on experimental measurements and/or a model). Under the assumption that the location, size, and geometry of the body-surface electrodes to be used during measurement are known, the dielectric coefficient values assigned to different tissues in the pre-acquired image are used to create a personalized 3D simulation of the electrical fields and/or field-related parameters such as voltage and impedance within the body of the patient using the pre-acquired image.

The mapping transformation is optionally generated based on the electrical readings received from locations within the heart, and the simulation data. The mapping transformation is generated using a non-rigid transformation algorithm that maps the electrical readings from the catheter to the estimations of the electrical reading data (e.g., the simulation data), and/or using a non-rigid transformation algorithm that maps the estimations of the simulated electrical reading data to the actual electrical readings received from the electrode(s) on the catheter.

Optionally, different phases of the respiratory cycle and/or cardiac cycle are simulated. For example, a library of images taken at different portions of the respiratory cycle and/or cardiac cycle may be pre-acquired. The electrical readings may be registered to an image acquired at the same portion of the cycle. Then, the image and the markings may be registered to an image of a reference portion of the cycle. This way, the operator is presented with a constant image, of the heart in the reference portion of the cycle, but the readings-to-locations transformation is based on readings taken and image acquired at different portions of the cycle. This way the library of images taken at different portion of the respiratory and/or cardiac cycle is created and used in real time during the treatment procedure, to improve the accuracy of displaying the anatomical location of the catheter within the pre-acquired imaging data.

Alternatively or additionally, the mapping transformation (for transforming the electrical readings to the anatomically corresponding image point(s)) is generated based on a "calculated correspondence" that maps point(s) on the pre-acquired image to the electrical readings, and using the inverse of the calculated correspondence (e.g., matrix) to generate the mapping from the electrical readings back to the pre-acquired image. The calculated correspondence from the image to the electrical readings is based on the observation by the inventors that the pre-acquired image contains a more complete set of data than the electrical readings, and therefore the calculated correspondence may be more easily and/or more accurately computed. Moreover, calculating the correspondence from the image to the electrical readings first may prevent erroneous fold back and/or artifacts, for example, that may occur in a region with tortuous vessels.

Alternatively or additionally, the mapping function is generated based on electrical readings received from multiple electrodes mounted on a static catheter. The static catheter may be a different catheter than the catheter used to navigate the interior of the heart, and/or may be the same as the navigation catheter that is currently being held stationary. The static catheter is located inside a known organ-region (e.g., coronary sinus of the heart) of the patient (or at another fixed positioned within the heart, or within another fixed position in the body of the patient).

The mapping function is generated based on a mapping from the electrical readings received from the electrodes mounted on the static catheter to image points in the pre-acquired 3D image that correspond to the locations where the catheter was held statically. For example, when the catheter is held stable in the known organ-region (e.g., coronary sinus), the mapping function is generated based on a requirement to transform readings received from within the known organ-region (e.g., coronary sinus) parameter to points located within the part of the 3D image that images the known organ-region (e.g., coronary sinus). The known location of the static catheter improves the accuracy of the generated mapping function. The generated mapping function may be used to create the transformation mapping. The generated mapping function may map new electrical readings from the catheter being maneuvered within the organ (e.g., heart) and/or outside the organ and/or including outside the known organ-region (e.g., coronary sinus).

At 110, the electrical reading(s) are transformed to one or more anatomical corresponding image points in the pre-acquired 3D image using the generated mapping transformation. The generated mapping transformation may be applied to map the electrical reading(s) to the anatomically corresponding image point(s) in the image. For example, when the generated mapping transformation is implemented as a matrix (e.g., a set of coefficient values) and the electrical readings are implemented as a vector, the matrix is multiplied by the vector to obtain the anatomical corresponding image point(s).

At 112, the pre-acquired 3D image is displayed on a display with a marking at an image point anatomically corresponding to a point where the catheter is located. As the catheter moves, the marking moves with it. The marking may include, for example, a color code (e.g., different than the color of the pre-acquired image), an arrow, a graphic representing the catheter, or other representations.

As used herein, the terms presented (or for presentation) and displayed (or for display) may be interchanged.

The pre-acquired 3D image may be presented from different vantage points. For example, the pre-acquired 3D image may be presented using an endoscopic view, in which the internal walls of the vessel lumen and/or the chamber are visible. The 3D image may be presented without the blood, allowing the user to view the internal contour of the vessel and/or chamber wall.

Optionally, a graphic overlay is presented on the 3D image according to the location of one or more image points. For example, the graphic overlay may be presented on the 3D image according to the image point representing the current location of the catheter within the organ, according to a point on an organ wall towards which the catheter is aimed, etc. For example, the graphic overlay may include a bull's eye image representing the region of ablation. The bull's eye may be centered according to the current location of the catheter. The bull's eye is dynamically repositioned within the 3D image according to the current location of the catheter within the organ.

The graphic overlay may be morphed according to the portion of the 3D organ below the image overlay, for example morphed for overlaying over a curved surface (e.g., inner contour of a vessel wall). The morphing may be dynamically performed as the catheter is moved, according to the underlying region of the 3D image corresponding to the image points denoting the current position of the catheter.

In some embodiments, the target is overlaid on the internal contour of the vessel and/or chamber according to a predefined location (e.g., the target is fixed on the image), with the location of the image point(s) being marked according the physical location of the catheter. The image point representing the catheter tip may be moved around the target as the catheter is moved, for example, to position the image point within a location in the target. It is noted that other graphical overlays may be implemented, for example, a cross, a square, a pointing arrow, an image of a catheter tip, and the like.

Figure 4A:
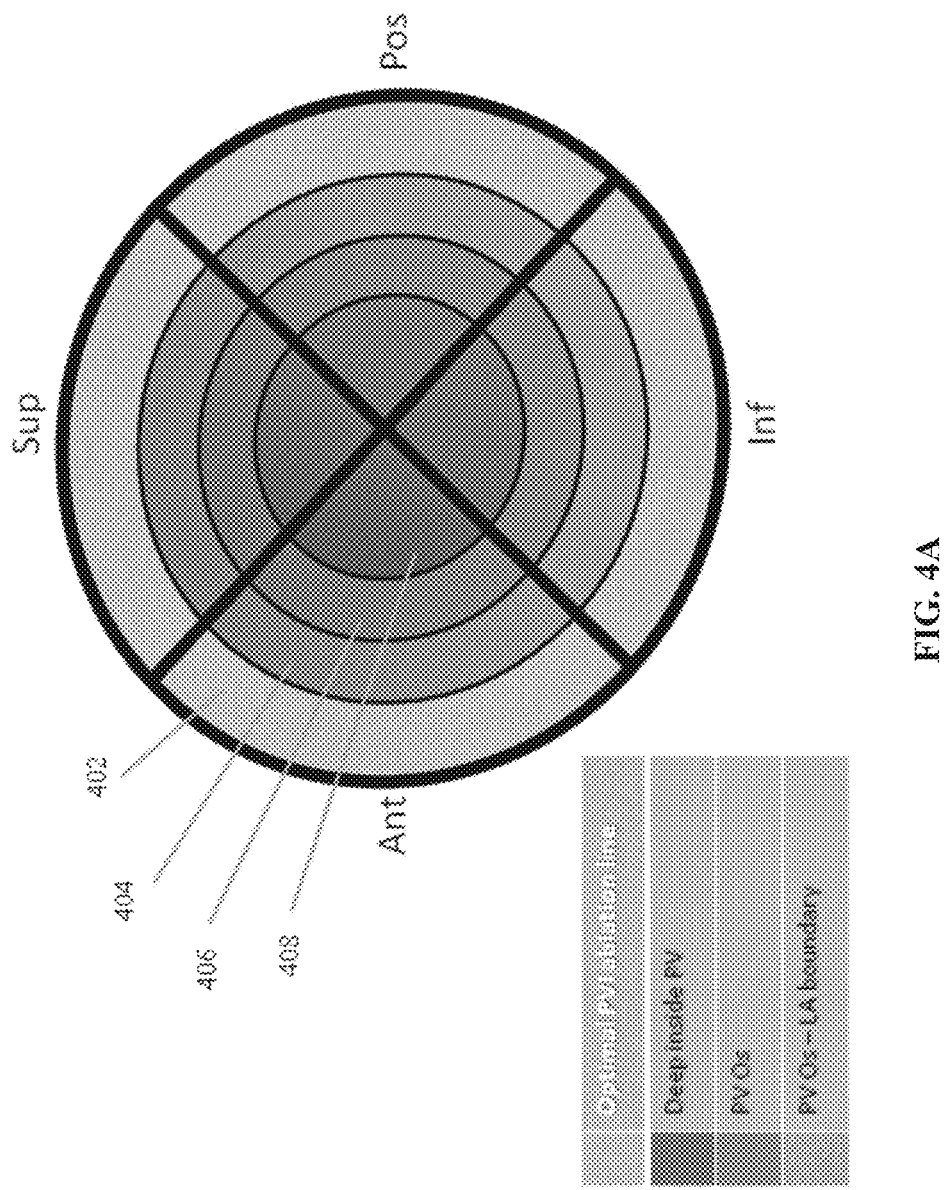
FIGS. 4A-4C are schematics of exemplary graphic overlays for presentation on the pre-acquired 3D image according to the location of the anatomical corresponding image point(s), in accordance with some embodiments of the present invention.
Figure 4B:
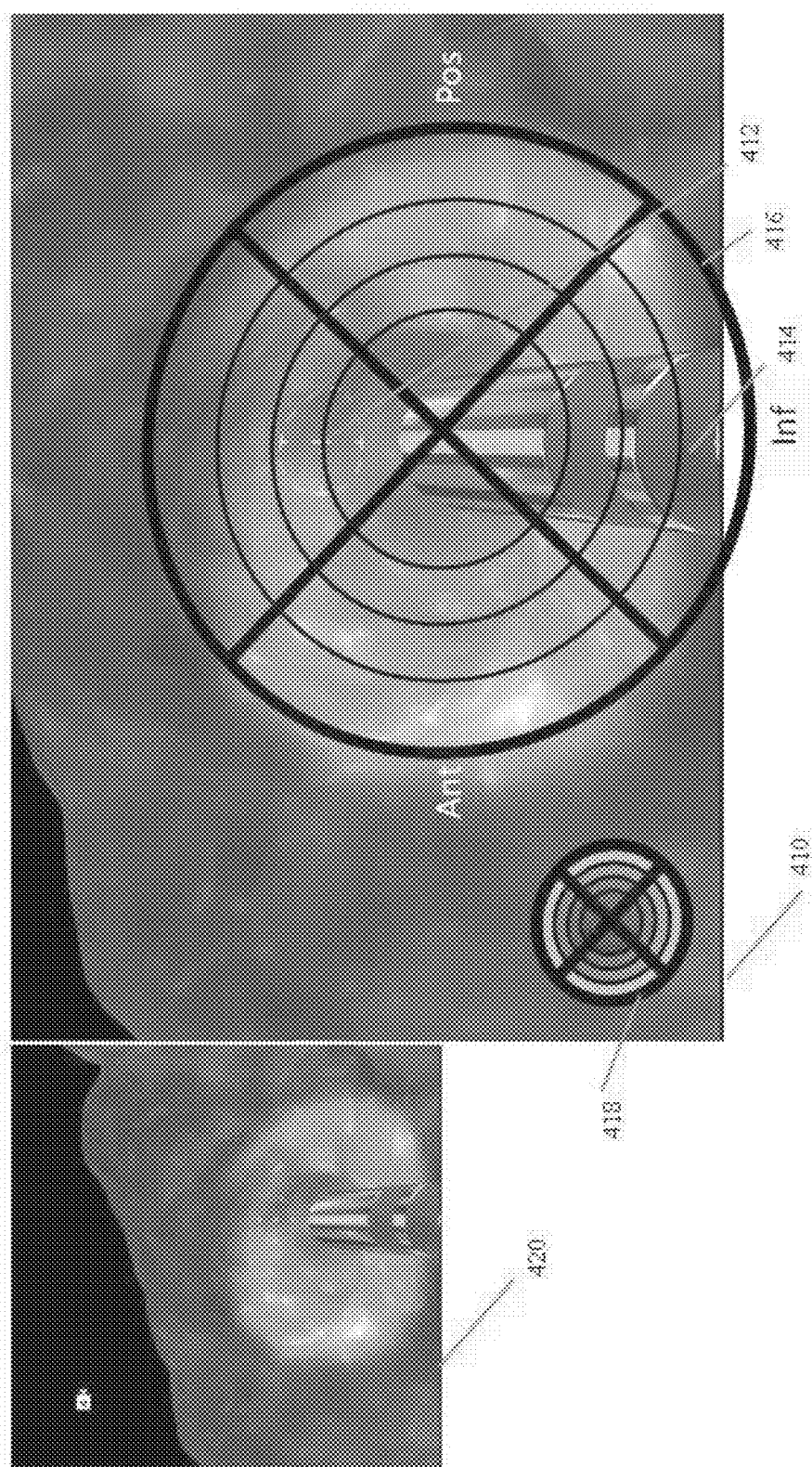
Figure 4C:
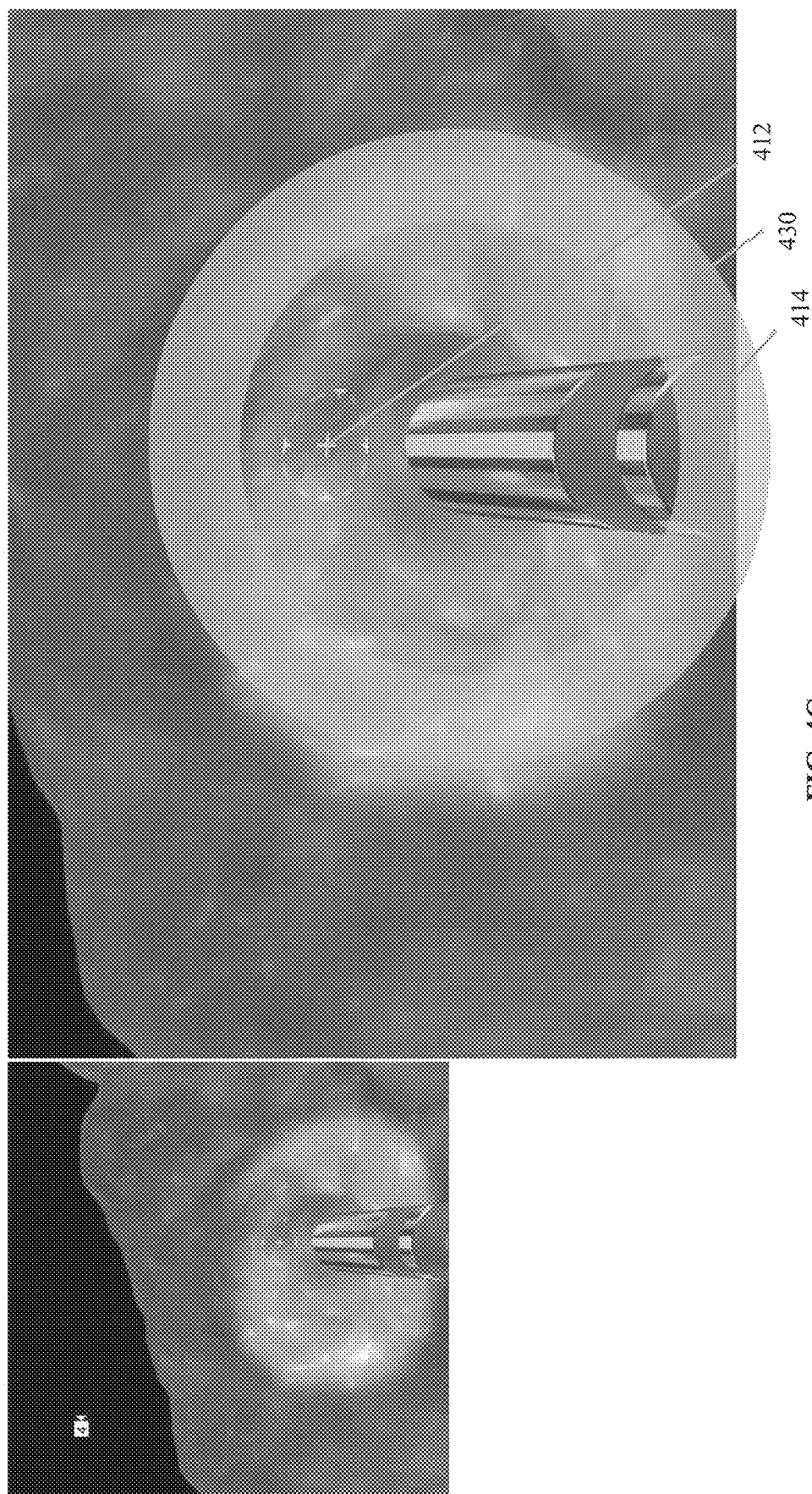

Reference is now made to FIGS. 4A-4C, which are schematics of exemplary graphic overlays for presentation on the pre-acquired 3D image, in accordance with some embodiments of the present invention.

FIG. 4A depicts an exemplary graphic overlay of a circular target bull's eye, including a cross. The target is designed to assist the operator in performing a pulmonary vein ablation procedure. The target is designed to be overlaid on the pulmonary vein ostium, optionally during an endoscopic view. The target may be color coded, which each color of each ring providing a layer of information to the operator. For example, outer ring 402 may represent the optimal pulmonary vein isolation (PVI) ablation line. Inner ring 404 represents the pulmonary vein ostium (PVO)-left atrium (LA) boundary. Inner ring 406 represents the pulmonary vein ostium. Circle 408 represents a region deep inside the PV.

FIG. 4B depicts image 410 that shows a pre-acquired image from an endoscopic view. The image is of an anatomical region including the pulmonary vein ostium Image point 412, which anatomically corresponds to the point on the wall towards which catheter 414 is pointing, is marked on the image. Target 416 (e.g., as described with reference to FIG. 4A, shown as color coded reference overlay 418) is overlaid on the image of the pulmonary vein ostium. The location of image point 412 is adjustable within target 416 by the user moving the real catheter within the heart of the patient. The operator may maneuver the catheter to position image point 412 within the optimal ablation location as shown by target 416.

An image 420 that includes a graphic of the catheter and a marking of the image point on the pre-acquired image without the target overlay may be presented instead of, or in addition to image 410, for example, to provide the operator with an image with the target and a corresponding image without the target.

FIG. 4C depicts another implementation of the presented image similar to image 420 of FIG. 4B, in which the graphic overlay is shown as a colored ring 430 depicting the recommended region for performing PVI ablation.

Referring now back to FIG. 1, at 114, acts described with reference to blocks 104-112 are iterated. The iteration may be performed for a new electrical reading, to transform the new electrical reading to a point on the image using the beforehand generated mapping transformation, and display the 3D image with a marking of the new image point. In some embodiments, the newly arriving readings are added to the readings processed in the preceding iteration, and all the readings are transformed, so that the transformation as a whole is updated by the newly arriving readings.

Alternatively or additionally, the new mapping transformation (and/or update of the mapping transformation) is generated using the new electrical reading. The new electrical reading is transformed to a new image point using the new mapping transformation, and the 3D image is displayed with a marking at the new image point.

Generating the new mapping transformation and/or updating the mapping transformation adjusts the transformation to changes in the heart morphology that occur over time during a treatment session, for example, due to changes in the breathing of the patient, volume changes in the patient, changes in the cardiac cycle, and/or changes to the heart structure resulting from the treatment (e.g., contraction due to ablation). It is noted that in contrast, other methods deteriorate as the procedure becomes longer.

Optionally, the mapping transform is updated using the new electrical reading, and/or a new mapping function is generated using the new electrical reading. The initial mapping transform may be calculated based on a limited (e.g., small) number of electrical readings, which may be based on the amount of time the operator spent performing an initial fast mapping of the target region (e.g., the internal wall of the chamber of the heart). The initial mapping transform is based on the number of electrical readings obtained, the location of the electrical readings, and the volumetric and/or geometric completeness of the initial set of readings (i.e., the initial V cloud). The initial mapping transform may be based on the mapping style used by the operator (e.g., continuous maneuver of the catheter while mostly touching the endocardial surface in a detailed paint brush like manner with subtle movements, or in contrast a more staccato like, acceleration-deceleration rich maneuver with sudden movements).

The initial mapping transformation may be updated as additional electrical readings are accumulated. The update and/or accumulation of electrical readings may be performed automatically, in the background, optionally using readings that are continuously collected and/or collected when the catheter is being moved. The updating may incrementally improve the accuracy of the mapping transformation. The update of the mapping transformation may be performed according to a noise parameter that defines an acceptable accuracy. The noise parameter may be initialized to incrementally higher values (e.g., continuously, step-wise, in a soft manner) during the update process. Setting the value of the noise parameter to incrementally higher values incrementally improves the accuracy of the update.

Optionally, the new electrical reading is from a second part of the heart, which is different from the first part of the heart used to generate the initial mapping transformation. For example, the first and second parts of the heart are selected from right atrium (RA), left atrium (LA), right ventricle (RV), left ventricle (LV), and aorta.

Thus, in an exemplary embodiment, a first part of the heart is mapped, and a transform is generated. This transform may then use for transforming readings from a second part of the heart for registering them with a pre-acquired image of the second part of the heart. For example, the right atrium may be mapped, and then the catheter may be moved (e.g., via a PFO or a transseptal puncture) to the left atrium, and the same transformation may be used for showing the catheter in the left atrium on a pre-acquired image of the left atrium.

Optionally, the readings from the first defined organ-region (e.g., coronary sinus) are obtained by one catheter positioned within the first defined organ-region. At least some readings from the first defined organ-region may denote a static measurement, optionally measured when the catheter is static within the first defined organ-region. It is noted that the static measurements may be obtained by the ablation catheter, for example, to reach a clearly defined target region for ablation and remain static at the target region. Another catheter is positioned within the second organ-region being mapped. The two catheters are optionally simultaneously positioned within the respective organ-regions. It is noted that the two catheters should be positioned close to one another for the transformation function computed based on the electrical readings of the first catheter within the first defined organ-region to be meaningful when applied to the electrical readings obtained from the second catheter within the second organ-region being mapped.

In some embodiments, the transformation function is computed based on readings obtained from the first organ-region by the first catheter, and applied to perform an initial transformation of electrical readings obtained from the second catheter located in the second organ-region. It is noted that the transformation function includes a large number of points (e.g., thousands) rather than a limited number of static points.

In an example, the transformation function computed based on electrical readings obtained by a catheter positioned in the right atrium may be used to compute the initial transformation of electrical readings obtained from another catheter positioned within the left atrium. For example, within the first about 30 seconds or within about the first minute after the second catheter enters the left atrium, navigation within the left atrium may be performed based on electrical readings obtained by electrodes of the second catheter, which are transformed into image points based on the transformation functions computed according to electrical readings of the first catheter within the right atrium. The initial transformation function (computed based on electrical readings obtained by the first catheter positioned in the right atrium) may be improved based on the electrical readings obtained by the electrodes of the second catheter within the left atrium (as described herein).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant images and catheters will be developed and the scope of the terms image and catheter are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of displaying a pre-acquired three dimensional (3D) image of at least a portion of an organ of a patient, the method comprising:
   accessing the pre-acquired 3D image representing the portion of the organ;
   receiving a plurality of electrical readings, the electrical readings being distorted, relative to image points in the pre-acquired 3D image, at least by inhomogeneity of the dielectric properties of different body tissues, and wherein the plurality of electrical readings includes electrical reading from a plurality of electrodes mounted on a catheter inside the portion of the organ of the patient, and wherein the plurality of electrodes are mounted on the catheter at known distances from each other;
   generating a mapping transformation, the generating comprising:
      assigning probabilities of correspondences between positions indicated by individual electrical readings and elements of the pre-acquired 3D image, and
      adjusting the positions indicated by the electrical readings from initial positions towards new positions, the new positions being closer to positions of elements of the pre-acquired 3D image with respectively larger probabilities of correspondence,
      wherein the adjusting is constrained by the known distances;
   transforming the plurality of electrical readings to a corresponding plurality of image points, using the mapping transformation; and
   displaying a representation of the portion of the organ, the displayed representation being generated using image data of the pre-acquired 3D image, and the displayed representation including a marking that:
      represents at least one of the plurality of image points, and
      is in a position of the displayed representation corresponding with the at least one of the plurality of image points.

2. The method of claim 1, wherein the location of the at least one of the plurality of image points is maintained relative to the 3D image during changes to the location of the electrodes relative to an external reference coordinate system, if the location of the electrodes does not change in relation to the anatomy of the at least a portion of the organ.

3. The method of claim 1, wherein the mapping transformation is computed independently of a static inertial coordinate system and of manually positioned landmark points.

4. The method of claim 1, further comprising:
   receiving a new electrical reading;
   transforming the new electrical reading to a new anatomically corresponding image point using the mapping transformation; and
   displaying the 3D image with a marking of the new anatomically corresponding image point.

5. The method of claim 4, wherein the mapping transformation is a transformation generated based on electrical readings all from a first part of the organ; and
   the new electrical reading is from a second part of the organ, different from the first part of the heart.

6. The method of claim 5, wherein the organ comprises a heart and each of the first and second parts of the heart is selected from the group consisting of: right atrium (RA), left atrium (LA), right ventricle (RV), left ventricle (LV), and aorta.

7. The method of claim 1, further comprising:
   receiving a new electrical reading;
   generating a new mapping transformation using the new electrical reading;
   transforming the new electrical reading to a new anatomically corresponding image point using the new mapping transformation; and
   displaying the 3D image with a marking at the new image point.

8. The method of claim 1, wherein the mapping transformation is generated based on a probabilistic correspondence model that defines the correspondence between the electrical readings and points of the pre-acquired image as a probability.

9. The method of claim 8, wherein the probabilistic correspondence model is optimized while respecting the known distances between the electrodes that acquired the electrical readings.

10. The method of claim 7, wherein the mapping transformation is generated by performing:
    receiving image data representing the 3D image;
    receiving electrical readings from the catheter at multiple points inside the organ of the patient; and
    generating the mapping transformation based on the image data and the electrical readings.

11. The method of claim 7, wherein the mapping transformation is generated by performing:
    receiving electrical readings from the catheter at multiple points inside the organ of the patient;
    receiving estimations of electrical reading data for points inside the 3D image; and
    generating the mapping transformation based on the electrical readings, and the estimations of electrical reading data.

12. The method of claim 11, wherein the mapping transformation is generated based on a non-rigid transformation algorithm to map electrical readings from the catheter to the estimations of electrical reading data, and/or using a non-rigid transformation algorithm to map the estimations of electrical reading data to the electrical readings from the catheter.

13. The method of claim 11, wherein the estimations of electrical reading data are based on a simulation, the simulation being based on the 3D image.

14. The method of claim 1, further comprising:
    monitoring breathing movements of the patient; and
    correcting the electrical reading from the electrode mounted on the catheter inside the portion of the organ of the patient based on the breathing movements to obtain corrected electrical readings.

15. The method of claim 14, wherein transforming electrical readings comprises transforming a plurality of corrected electrical readings.

16. The method of claim 1, wherein the electrical readings include readings of potential difference between the electrode inside the organ and pad-electrodes attached to the outer surface of the patient.

17. The method of claim 16, wherein:
    electrical readings are normalized to a potential difference between two of the pad-electrodes to obtain normalized electrical readings; and
    transforming the electrical readings includes transforming the normalized electrical readings.

18. The method of claim 1, further comprising:
receiving electrical readings from multiple electrodes mounted on a static catheter inside a defined first organ-region of the patient;
generating a mapping function mapping the electrical readings received from the multiple electrodes mounted on the static catheter to points in the 3D image, the points being in a part of the 3D image that images the first organ-region; and
using the mapping function to generate the mapping transformation that transforms an electrical reading of the catheter from inside a second organ-region of the patient to an anatomically corresponding image point in the 3D image.

19. The method of claim 1, wherein the transforming is preformed based on the electrical readings with no use of manual registration between electrical readings and image points.

20. The method of claim 1, further comprising correcting the pre-acquired 3D image according to the electrical readings, wherein the imaged portion of the organ of the corrected pre-acquired 3D image corresponds to the actual current anatomy of the imaged portion of the organ from which the electrical readings are obtained.

21. The method of claim 20, wherein the correction of the pre-acquired 3D image is performed so that a distance between two given electrodes is constant across the corrected 3D image.

22. The method of claim 20, wherein portions of the pre-acquired 3D image, imaging tissue external to the portion of the organ where the electrical readings are obtained are transformed according to the electrical readings obtained from the inside of the portion of the organ where the electrical readings are obtained.

23. A system for displaying a pre-acquired three dimensional (3D) image of at least a portion of a heart of a patient, the system comprising:
an electrical interface for receiving electrical readings from a plurality of electrode mounted on a catheter inside the portion of the organ of the patient; the plurality of electrodes being mounted on the catheter at known distances from each other;
a program store storing code; and
at least one processor coupled to the electrical interface and the program store for implementing the stored code, the code comprising:
code to generate a mapping transformation by:
assigning probabilities of correspondences between positions indicated by individual electrical readings and elements of the pre-acquired 3D image, and
adjusting the positions indicated by the electrical readings from initial positions towards new positions, the new positions being closer to positions of elements of the pre-acquired 3D image with respectively larger probabilities of correspondence,
wherein the adjusting is constrained by the known distances;
code to transform the electrical readings to an image point in the pre-acquired 3D image using the mapping transformation to transform each electrical reading of the catheter from inside the portion of the organ of the patient to an anatomically corresponding image point in the pre-acquired 3D image; and
code to display the pre-acquired 3D image with a marking at the image point.

24. The system of claim 23, wherein the mapping transformation is computed independently of a static inertial coordinate system and of manually positioned landmark points.

25. The system of claim 23, further comprising code for:
monitoring breathing movements of the patient; and
correcting the electrical reading from the electrode mounted on the catheter inside the portion of the organ of the patient based on the breathing movements to obtain corrected electrical readings.

26. The system of claim 25, wherein transforming electrical readings comprises transforming a plurality of corrected electrical readings.

27. A method of displaying a pre-acquired three dimensional (3D) image of at least a portion of an organ of a patient, the method comprising:
receiving an electrical reading from an electrode mounted on a catheter inside the portion of the organ of the patient;
transforming the electrical reading to an image point in the pre-acquired 3D image using a mapping transformation that transforms each electrical reading of the catheter from inside the portion of the organ of the patient to an anatomically corresponding image point in the pre-acquired 3D image; and
displaying the pre-acquired 3D image with a marking at the image point.

28. The method of claim 27, further comprising:
receiving a plurality of electrical readings, each from a different electrode mounted on the catheter, wherein the electrodes are mounted on the catheter at known distances from each other; and
transforming the plurality of electrical readings to a corresponding plurality of image points using a mapping transformation that transforms each electrical reading of the catheter from inside the portion of the organ of the patient to an anatomically corresponding image point in the 3D pre-acquired image based on the known distances.

29. A method of displaying a pre-acquired three dimensional (3D) image of at least a portion of an organ of a patient, the method comprising:
receiving a plurality of electrical readings, the plurality of electrical readings including electrical readings from electrodes mounted on a catheter inside the portion of the organ of the patient, wherein the electrodes are mounted on the catheter at known distances from each other;
generating a mapping transformation, the generating comprising:
assigning probabilities of correspondences between positions indicated by individual electrical readings and elements of the pre-acquired 3D image, and
adjusting the positions indicated by the electrical readings from initial positions towards new positions, the new positions being closer to positions of elements of the pre-acquired 3D image with respectively larger probabilities of correspondence,
wherein the adjusting is constrained by the known distances;
transforming the plurality of electrical readings to a corresponding plurality of image points, using the mapping transformation; and
displaying the 3D image with a marking at at least one of the plurality of image points.

30. The method of claim 29, comprising accessing the pre-acquired 3D image, the pre-acquired 3D image being obtained using an imaging modality selected from the list consisting of: computer tomography, ultrasound, nuclear magnetic resonance, and single photon emission computer tomography.

* * * * *